US008285377B2

(12) United States Patent
Rosenberg et al.

(10) Patent No.: US 8,285,377 B2
(45) Date of Patent: Oct. 9, 2012

(54) PACING, SENSING AND OTHER PARAMETER MAPS BASED ON LOCALIZATION SYSTEM DATA

(75) Inventors: Stuart Rosenberg, Castaic, CA (US);
Kyungmoo Ryu, Palmdale, CA (US);
Allen Keel, San Francisco, CA (US);
Wenbo Hou, Lancaster, CA (US); Thao Thu Nguyen, Bloomington, MN (US);
Steve Koh, South Pasadena, CA (US);
Kjell Noren, Solna (SE); Michael Yang, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 542 days.

(21) Appl. No.: 12/553,413

(22) Filed: Sep. 3, 2009

(65) Prior Publication Data
US 2011/0054559 A1 Mar. 3, 2011

(51) Int. Cl.
*A61N 1/362* (2006.01)
(52) U.S. Cl. .......................................... 607/28
(58) Field of Classification Search ...................... 607/28
See application file for complete search history.

(56) References Cited

U.S. PATENT DOCUMENTS

| | | | |
|---|---|---|---|
| 5,687,737 A | 11/1997 | Branham et al. | |
| 6,782,291 B1 | 8/2004 | Bornzin et al. | |
| 7,082,330 B2 | 7/2006 | Stadler et al. | |
| 7,613,500 B2 | 11/2009 | Vass et al. | |
| 2002/0183795 A1 | 12/2002 | Rouw et al. | |
| 2005/0149138 A1 | 7/2005 | Min et al. | |
| 2007/0123944 A1 | 5/2007 | Zdeblick | |
| 2007/0135721 A1 | 6/2007 | Zdeblick | |
| 2007/0156196 A1 | 7/2007 | Kim et al. | |
| 2008/0058656 A1 | 3/2008 | Costello et al. | |
| 2008/0183072 A1 | 7/2008 | Robertson et al. | |
| 2008/0242976 A1 | 10/2008 | Robertson et al. | |
| 2009/0018632 A1 | 1/2009 | Zdeblich et al. | |
| 2009/0093857 A1 | 4/2009 | Markowitz et al. | |
| 2010/0198292 A1* | 8/2010 | Honeck et al. | 607/17 |

FOREIGN PATENT DOCUMENTS

| | | |
|---|---|---|
| WO | 2006042039 A2 | 4/2006 |
| WO | 2006042039 A3 | 4/2006 |
| WO | 2007111542 A1 | 10/2007 |
| WO | 2007120290 A2 | 10/2007 |
| WO | 2007120290 A3 | 10/2007 |

OTHER PUBLICATIONS

Chen, Ruo-han et al., "Impact of automatic threshold capture on pulse generator longevity," Chin Med J. 2006;119(11):925-929.
NonFinal Office Action mailed, Feb. 2, 2012; U.S. Appl. No. 12/553,473.
Final Office Action mailed, Jul. 10, 2012; U.S. Appl. No. 12/553,473.

* cited by examiner

*Primary Examiner* — Eric D. Bertram

(57) ABSTRACT

An exemplary method generates a map of a pacing parameter, a sensing parameter or one or more other parameters based in part on location information acquired using a localization system configured to locate electrodes in vivo (i.e., within a patient's body). Various examples map capture thresholds, qualification criteria for algorithms, undesirable conditions and sensing capabilities. Various other methods, devices, systems, etc., are also disclosed.

10 Claims, 12 Drawing Sheets

PACING, SENSING AND OTHER PARAMETER MAPS BASED ON LOCALIZATION SYSTEM DATA

CROSS-REFERENCE TO RELATED APPLICATIONS

This application is related to copending U.S. patent application Ser. No. 12/553,473, filed concurrently herewith, titled "Pacing, Sensing and Other Parameter Maps Based on Localization System Data".

TECHNICAL FIELD

Subject matter presented herein relates generally to cardiac pacing and/or stimulation therapy. Various examples map one or more parameters based, at least in part, on data acquired using a localization system.

BACKGROUND

Cardiac resynchronization therapy (CRT) aims to improve cardiac performance by synchronizing the ventricles. While the term "synchronization" is used, for some patients, a delay between contraction of the right ventricle and the left ventricle may be optimal. Hence, the term synchronization refers more generally to ventricular timing that improves cardiac performance. A general objective measure of lack of synchrony or dyssynchrony is QRS width representative of contraction of both ventricles. For example, a QRS width greater than about 130 ms may indicate dysynchrony.

CRT can improve a variety of cardiac performance measures including left ventricular mechanical function, cardiac index, decreased pulmonary artery pressures, decrease in myocardial oxygen consumption, decrease in dynamic mitral regurgitation, increase in global ejection fraction, decrease in NYHA class, increased quality of life scores, increased distance covered during a 6-minute walk test, etc. Effects such as reverse modeling may also be seen, for example, three to six months after initiating CRT. Patients that show such improvements are classified as CRT "responders". However, for a variety of reasons, not all patients respond to CRT. For example, if a left ventricular stimulation lead cannot locate an electrode in a favorable position, then a patient may not respond to CRT.

Often, the ability to respond and the extent of response to CRT depends on an initial set-up of a CRT device in a patient. As described herein, various exemplary technologies aim to improve a clinician's ability to set-up a CRT at implant and to optionally optimize thereafter. In particular, various exemplary techniques include mapping parameters based, at least in part, on information acquired from a localization system.

SUMMARY

An exemplary method generates a map of a pacing parameter, a sensing parameter or one or more other parameters based in part on location information acquired using a localization system configured to locate electrodes in vivo (i.e., within a patient's body). Various examples map capture thresholds, qualification criteria for algorithms, undesirable conditions and sensing capabilities. Various other methods, devices, systems, etc., are also disclosed.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
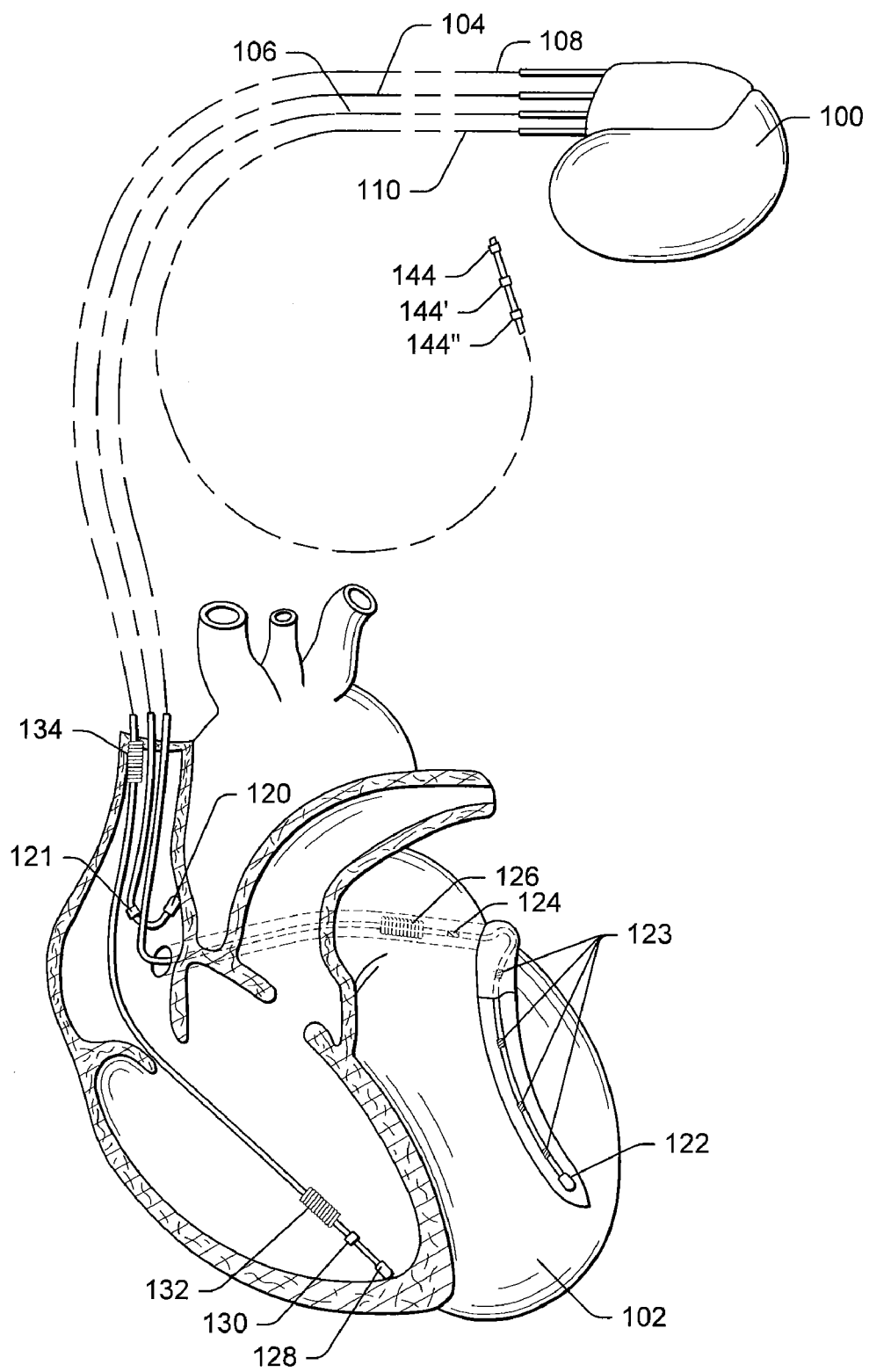
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

The following description includes the best mode presently contemplated for practicing the described implementations. This description is not to be taken in a limiting sense, but rather is made merely for the purpose of describing the general principles of various implementations. The scope of the described implementations should be ascertained with reference to the issued claims. In the description that follows, like numerals or reference designators are typically used to reference like parts or elements throughout.

Overview

Various exemplary techniques described herein pertain to multi-dimensional mapping of one or more parameters germane to cardiac pacing therapy (e.g., including CRT). For example, during an intraoperative procedure, a clinician may maneuver a catheter to various locations in one or more chambers or vessels of the heart and deliver energy at the various locations using one or more electrodes of the catheter. Sensing equipment may sense electrical signals responsive to the delivered energy and, in turn, a mapping application may associate the signals with the various locations. In a specific example, the level of energy delivered is varied and the sensed electrical signals are analyzed to determine a so-called capture threshold (e.g., a minimum level of energy required to cause a cardiac evoked response). In this specific example, the mapping application can generate a capture threshold map that can be used by a clinician to locate one or more electrodes chronically (e.g., for use by an implantable pacing device). In general, by pacing at a myocardial location with a low capture threshold, a clinician can reduce energy drain and increase longevity of an implantable pacing device. While capture threshold alone is mentioned, one or more other factors that can affect current drain may be considered (e.g., impedance of an electrode configuration).

In various examples, sensing may occur using one or more implantable sensors (e.g., including electrodes), external sensors (e.g., surface ECG, fluoroscopic, etc.), or a combination of implantable and external sensors. Hence, as described herein, as long as a location of "stimulation" or sensing is known, a map can be generated. With respect to "stimulation", this term may include stimulation, alteration or inhibition. For example, an electrode can be used to stimulate, alter or inhibit a response, a drug delivery mechanism can be used to stimulate, alter or inhibit a response, a heater or RF applicator can be used to stimulate, alter or inhibit a response, etc. With respect to sensing, this term may include electrical sensing (e.g., using electrodes) or use of actual sensors that act as transducers (e.g., to convert physical information to electrical signals). Hence, with respect to mapping, stimulation and sensing options can include: (i) implantable stimulation and sensing; (ii) implantable stimulation and external sensing; (iii) external stimulation and implantable sensing; and (iv) any combination of the foregoing options. According to these options, the implantable stimulation and sensing can be localized using a localization system.

Given the various options, an exemplary method can include mapping sensing parameters. For example, signal-to-noise ratio of features in an electrogram may be an important deciding factor for implementing a specific algorithm (e.g., arrhythmia discrimination, automatic capture threshold detection, etc.). During an intraoperative procedure, a clinician may maneuver a lead to various locations and sense intrinsic cardiac signals, evoked response signals, actual arrhythmia signals or induced arrhythmia signals. An analysis of one or more features of such signals may assign one or more corresponding signal-to-noise ratios to the locations. In turn, a mapping application can map the signal-to-noise ratio, optionally on a feature-by-feature basis. Upon display of such a map, a clinician may readily discern locations with suitable signal-to-noise ratios for chronic implantation of one or more sensors. For example, a clinician may aim to identify regions with suitable signal-to-noise rations for sensing P-waves, R-waves, far-field R-waves, evoked responses, etc. As described herein, enhanced signal-to-noise ratios can avoid under or oversensing, allow for implementation of various algorithms and make decisions by conventional algorithms more robust.

With respect to external sensing, such sensing need not necessarily rely on sensing equipment. For example, if a clinician seeks to avoid phrenic nerve stimulation by a delivery of ventricular stimulation energy, the clinician can merely record patient movement as witnessed visually. Or, the patient may be capable of responding to questions such that the information per the responses and the delivery locations can be mapped.

Various exemplary methods may be implemented, for example, using a pacing system analyzer (PSA) and a localization system or a specialized localization system. Various examples are described with respect to the ENSITE® NAVX® localization system; noting that other types of localization systems may be used.

Various techniques aim to facilitate lead implantation, particularly for leads that enter the coronary sinus to reach distal branches thereof. For example, a clinician can view a map of pacing parameters and readily decide to locate a lead in a region with appropriate pacing parameters. Parameters can include pacing capture threshold, pacing impedance, sense amplitude (P and/or R wave), and presence or absence of unwanted phrenic nerve capture. In an intraoperative environment, such parameters are often determined during movement of a catheter or a lead using un-localized measurements acquired by a pacing system analyzer (PSA). Thus, a typical process occurs iteratively (i.e., move, determine, assess; move, determine, assess; move, determine, assess; . . . ). In this iterative process, a clinician typically notes whether a position is acceptable or unacceptable (a binary question) and formal optimization of pacing parameters with respect to location is generally not performed. Hence, the conventional iterative process lacks assurances as to optimal location, which may result in implanting a lead at a site that requires higher current drain than other candidate sites, or a site that requires sub-optimal sensor settings in order to avoid inappropriate device diagnosis and therapy.

As described herein, various techniques can locate electrodes (or other "stimulators") and generate maps. Various techniques may operate in conjunction with one or more PSA functionalities, for example, to create and display maps that show variations in pacing, sensing or other parameters with respect to anatomic locations.

As described herein, various exemplary techniques can be used to make decisions as to cardiac pacing therapy and optimization of a cardiac pacing therapy (e.g., CRT or other pacing therapies). In a clinical trial, acute resynchronization was shown to be a significant factor in assessing CRT efficacy and long-term outcome[1]. Various methods described herein, build on this clinical finding by formulating specialized techniques and metrics (e.g., maps) associated with pacing and sensing. In turn, one or more of these metrics may be used to determine how effective a particular CRT therapy or configuration thereof is at time of implant or, in some instances, after implant.

[1] G B Bleeker, S A Mollema, E R Holman, N Van De Veire, C Ypenburg, E Boersma, E E van der Wall, M J Schalij, J J Bax. "Left Ventricular Resynchronization is Mandatory for Response to Cardiac Resynchronization Therapy: Analysis in Patients with Echocardiographic Evidence of Left Ventricular Dyssynchrony at Baseline". *Circulation* 2007; 116: 1440-1448.

An exemplary stimulation device is described followed by various techniques for acquiring and localizing information. The drawings and detailed description elucidate details of various distinct parameters that may be used singly or in combination during an assessment or an optimization process.

Exemplary Stimulation Device

The techniques described below are intended to be implemented in connection with any stimulation device that is configured or configurable to delivery cardiac therapy and/or sense information germane to cardiac therapy.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy and/or assessment of cardiac condition. As described in more detail below, an illustrative method acquires information using various electrode configurations where an electrode configuration typically includes at least one electrode of a coronary sinus lead or other type of left ventricular lead. Such information may be used to determine a suitable electrode configuration for the lead 106 (e.g., selection of one or more electrodes 123 of the lead 106).

An exemplary coronary sinus lead 106 can be designed to receive ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead. A right ventricular lead may include a series of electrodes, such as the series 123 of the left ventricular lead 106.

Figure 2:
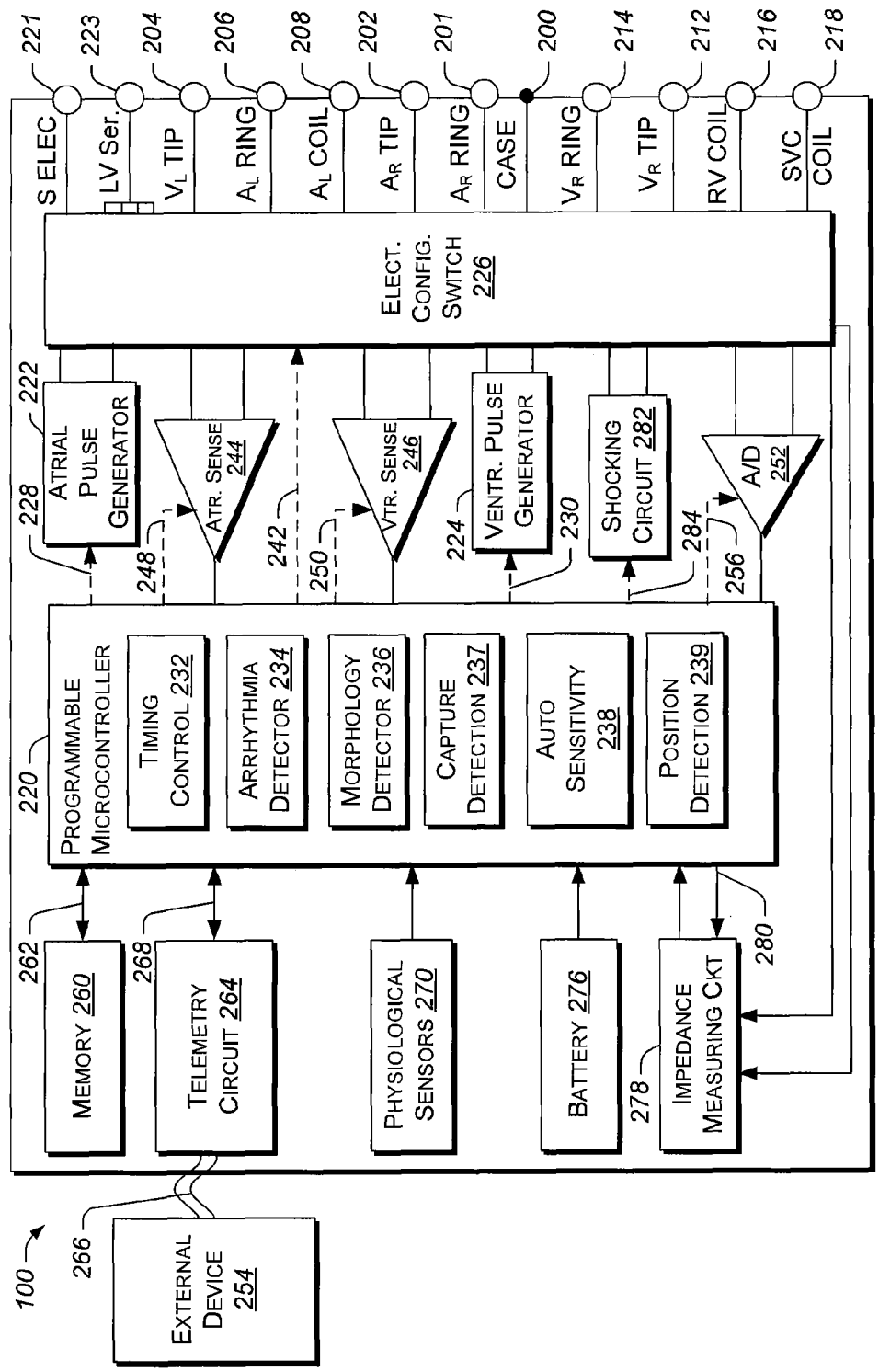
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art. As described herein, the microcontroller 220 operates according to control logic, which may be in the form of hardware, software (including firmware) or a combination of hardware and software. With respect to software, control logic instructions may be stored in memory (e.g., memory 260) for execution by the microcontroller 220 to implement control logic.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes an optional position detection module 239. The module 239 may be used for purposes of acquiring position information, for example, in conjunction with a device (internal or external) that may use body surface patches or other electrodes (internal or external). The microcontroller 220 may initiate one or more algorithms of the module 239 in response to a signal detected by various circuitry or information received via the telemetry circuit 264. Instructions of the module 239 may cause the device 100 to measure potentials using one or more electrode configurations where the potentials correspond to a potential field generated by current delivered to the body using, for example, surface patch electrodes. Such a module may help monitor position and cardiac mechanics in relationship to cardiac electrical activity and may help to optimize cardiac resynchronization therapy. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Figure 11:
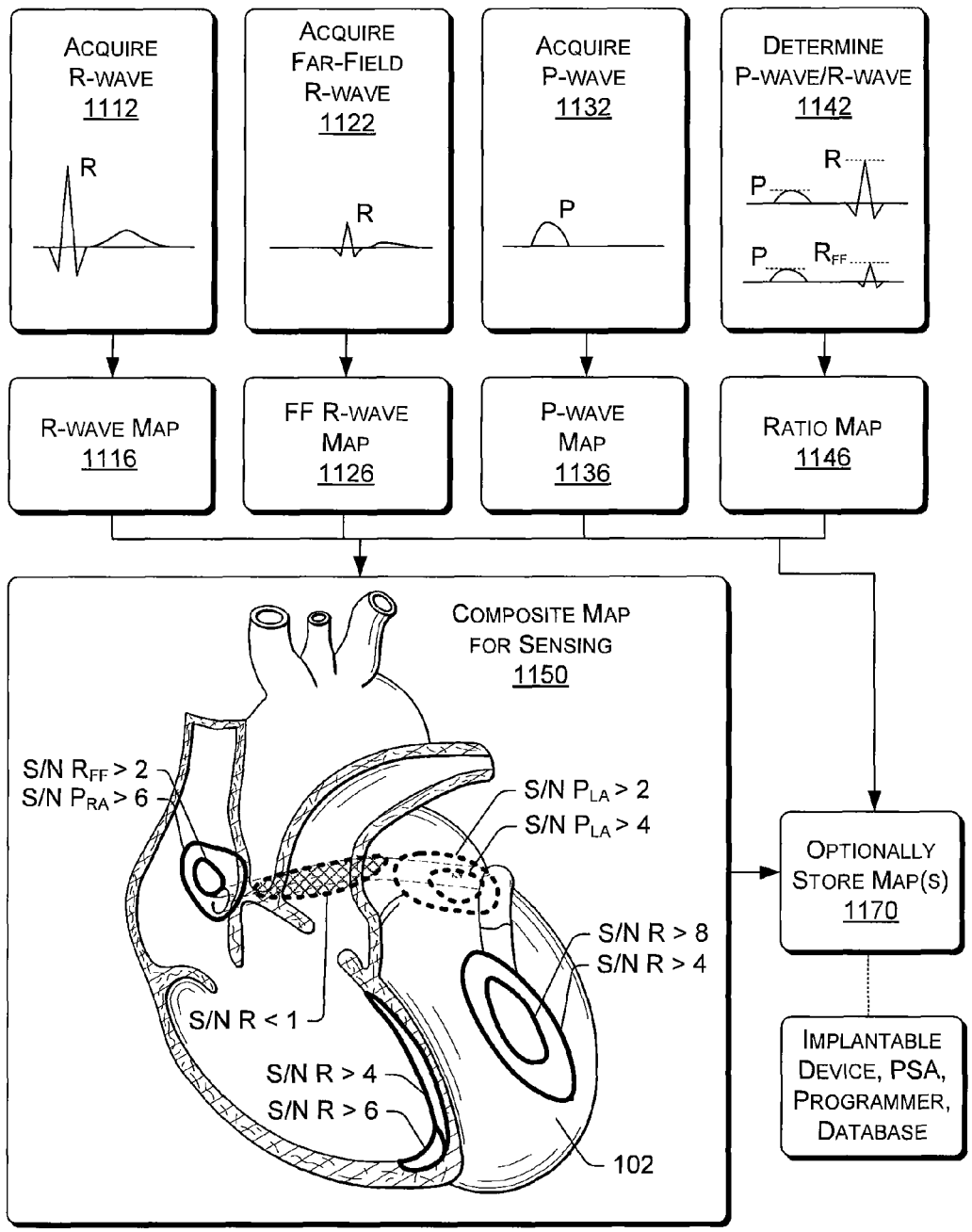
FIG. 11 is a block diagram of an exemplary method for mapping sensing information such as signal-to-noise ratio for sensing cardiac electrical signals, for example, corresponding to R-waves, P-waves, evoked responses, etc.

Cardiac signals are also applied to inputs of an analog-to-digital (A/D) data acquisition system 252. Additional configurations are shown in FIG. 11 and described further below. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes. A control signal 256 from the microcontroller 220 may instruct the A/D 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, where the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV delay, VV delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, where an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 $cm^2$) and/or higher current frequencies (e.g., above about 10 kHz) to reduce noise.

Figure 3:
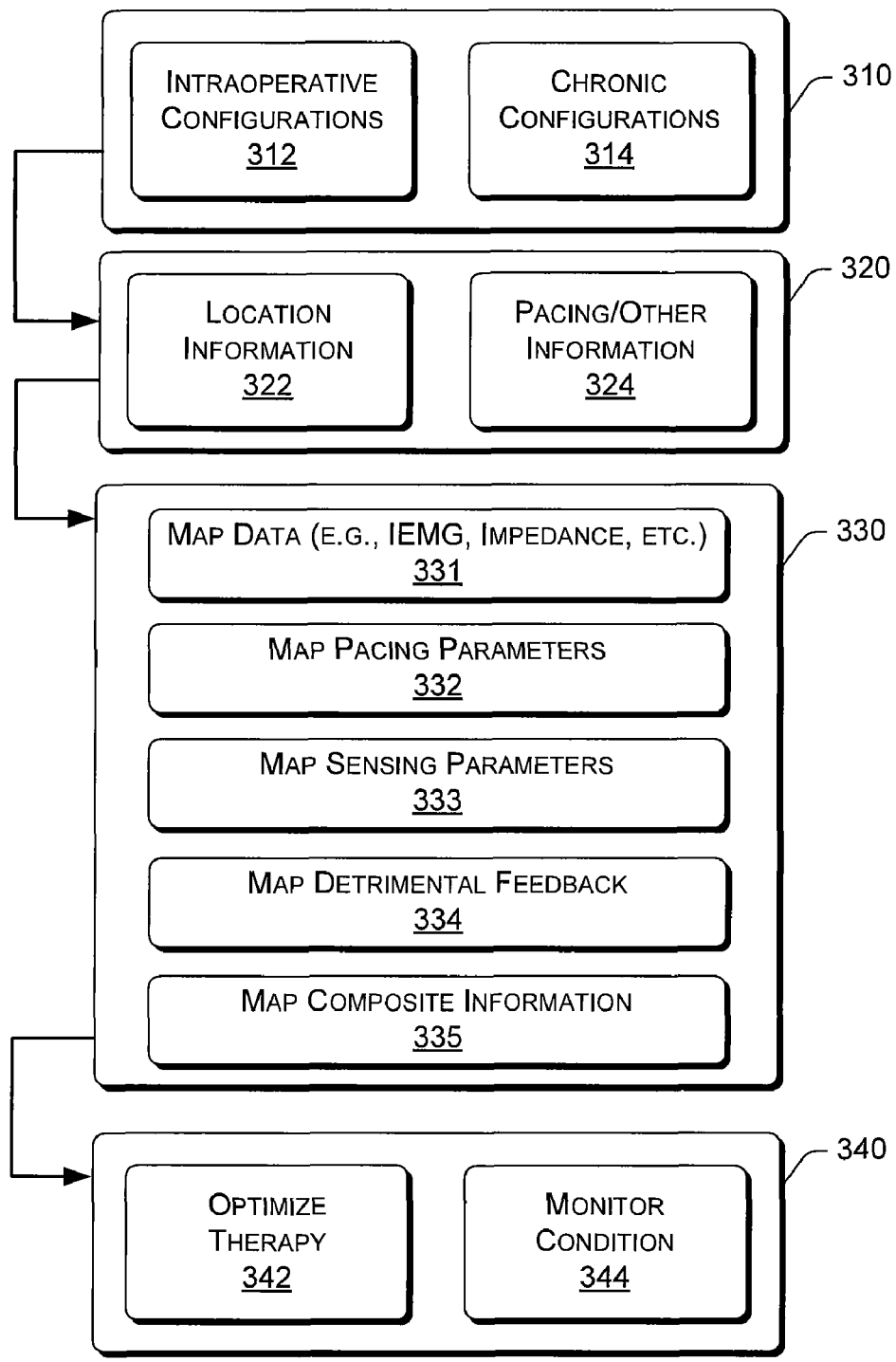
FIG. 3 is a block diagram of an exemplary method for optimizing therapy and/or monitoring conditions based at least in part on localized information.

FIG. 3 shows an exemplary method 300 for acquiring and mapping information. In the example of FIG. 3, the method 300 includes a configurations block 310 that includes intraoperative configurations 312 and chronic configurations 314. The intraoperative configurations 312 pertain to configurations that may be achieved during an operative procedure. For example, during an operative procedure, one or more leads (and/or catheter(s)) may be positioned in a patient where the one or more leads are connected to, or variously connectable to, a device configured to acquire information and optionally to deliver electrical energy to the patient (e.g., to the heart, to a nerve, to other tissue, etc.). The chronic configurations 314 pertain to configurations achievable by a chronically implanted device and its associated lead or leads. In general, intraoperative configurations include those achievable by physically re-positioning a lead (or catheter) in a patient's body while chronic configurations normally do not allow for re-positioning as a lead or leads are usually anchored during implantation or become anchored in the weeks to months after implantation. Chronic configurations do, however, include selection of a subset of the multiple implanted electrodes, for example using the tip electrode versus the first ring electrode as a cathode or using the tip and first ring as a bipolar pair versus using the tip and ring as two independent cathodes. Thus, intraoperative configurations include configurations available by changing device settings, electrode selection, and physical position of electrodes, while chronic configurations include only those configurations available by changing device settings and electrode selection, or "electronic repositioning" of one or more stimulation electrodes.

As indicated in FIG. 3, an acquisition block 320 includes acquisition of location information 322 and optionally acquisition of pacing and/or other information 324 (e.g., electrical information as to electrical activity of the heart, biosensor information, etc.). While an arrow indicates that a relationship or relationships may exist between the configurations block 310 and the acquisition block 320, acquisition of information may occur by using in part an electrode (or other equipment) that is not part of a configuration. For example, the acquisition block 320 may rely on one or more surface electrodes that define a coordinate system or location system for locating an electrode that defines one or more configurations. For example, three pairs of surface electrodes positioned on a patient may be configured to deliver current and define a three-dimensional space whereby measurement of a potential locates an electrode in the three-dimensional space.

As described herein, an electrode may be configured for delivery of energy to the heart; for acquisition of electrical information; for acquisition of location information; for acquisition of electrical information and location information; for delivery of energy to the heart and for acquisition of electrical information; for delivery of energy to the heart and for acquisition of location information; for delivery of energy to the heart, for acquisition of electrical information and for acquisition of location information.

In various examples, acquisition of location information occurs by measuring one or more potentials where the measuring relies on an electrode that assists in locating the electrode or other item where the electrode may also be configured to sense signals and/or deliver energy to the heart (e.g., electrical energy to pace a chamber of the heart). For example, an electrode may deliver energy sufficient to stimulate the heart and then be tracked along one or more dimensions to monitor the location information resulting from the stimulation. Further, such an electrode may be used to acquire electrical information (e.g., an IEGM that evidences an evoked response). Such an electrode can perform all three of these tasks with proper circuitry and control. For example, after delivery of the energy, the electrode may be configured for acquiring one or more potentials related to location and for acquiring an electrogram. To acquire potentials and an electrogram, circuitry may include gating or other sampling techniques (e.g., to avoid circuitry or interference issues). Such circuitry may rely on one sampling frequency for acquiring potentials for motion tracking and another sampling frequency for acquiring an electrogram.

The method 300 of FIG. 3 includes a mapping block 330 for mapping data 331, pacing parameters 332, sensing parameters 333, detrimental feedback 334 or composite information 335. These options are described in more detail further below.

As shown in the example of FIG. 3, the conclusion block 340 may perform actions such as to optimize therapy 342 and/or to monitor patient and/or device condition 344. These options are described in more detail with respect to FIG. 4.

Figure 4:
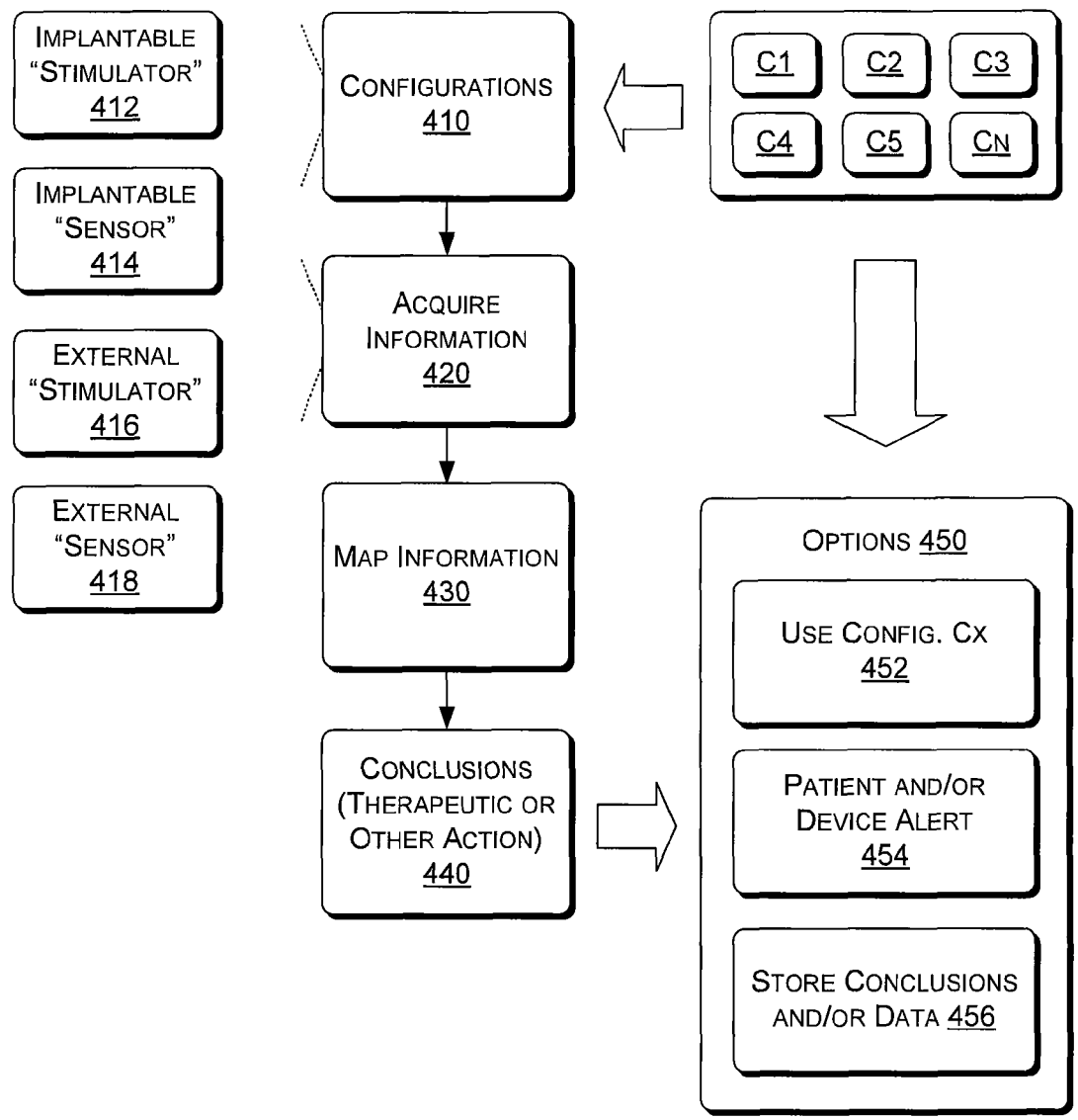
FIG. 4 is a block diagram of the exemplary method of FIG. 3 along with various options.

FIG. 4 shows an exemplary method 400 with various configurations 410 (C1, C2, . . . , Cn) and options 450. As mentioned, a configuration may be defined based on factors such as electrode position (e.g., with respect to some physiological feature of the heart or another electrode), stimulation parameters for an electrode or electrodes and, where appropriate, one or more interelectrode timings. Hence, with reference to FIG. 1, C1 may be a configuration that relies on the RV tip electrode 128, the RV ring electrode 130, the LV tip electrode 122 and the LV ring electrode 124 while C2 may be a configuration that relies on the same electrodes as C1 but where the stimulation polarity for the LV electrodes is reversed. Further, C3 may rely on the same electrodes where the timing between delivery of a stimulus to the RV and delivery of a stimulus to the LV is different compared to C1. Yet further, C4 may rely on the same electrodes where the duration of a stimulus to the RV is different compared to C1. In these foregoing examples, configurations provide for one or more electrodes to deliver energy to stimulate the right ventricle and for one or more electrodes to deliver energy to stimulate the left ventricle. In other examples, configurations may provide for stimulation of a single chamber at one or more sites, stimulation of one chamber at a single site and another chamber at multiple sites, multiple chambers at multiple sites per chamber, etc.

As mentioned, configurations can include one or more so-called "stimulators" and/or "sensors". As shown, the configurations block 410 may select a configuration that includes one or more of the following: an implantable stimulator 412, an implantable sensor 414, an external stimulator 416 and an external sensor 418. Regardless of the configuration, localization information is acquired for at least one implantable stimulator or at least one implantable sensor. Such a stimulator or a sensor can include one or more electrodes configured to measure a potential or potentials to thereby directly or indirectly locate the stimulator or the sensor. For example, a lead-based oximeter (oxygen sensor) may include an electrode configured to measure a potential for locating the oximeter or a lead-based RF applicator may include electrodes configured to measure potentials for locating the RF applicator or a tip of the lead.

In an acquisition block 420, acquisition occurs for location information where such information pertains to one or more configurations. In a map block 430, one or more maps are made based at least in part on the location information (see, e.g., the mapping block 330 of FIG. 3). A conclusions block 430 provides for therapeutic or other action, which may be selected from one or more options 450.

In the example of FIG. 4, the one or more options 450 include selection of a configuration 452 (e.g., Cx, where x is a number selected from 1 to n), issuance of a patient and/or device alert 454 that pertains to condition of a patient or a condition of a device or associated lead(s) or electrode(s), and storage of conclusion(s) and/or data 456. The options 450 may be associated with the configurations 410, as indicated by an arrow. For example, storage of conclusions and/or data 456 may also store specific configurations, a generalization of the configurations (e.g., one or more shared characteristics), a device/system arrangement (e.g., where the number and types of configurations would be known based on the arrangement), etc.

As described herein, an exemplary method can include: positioning one or more electrodes within the heart and/or surrounding space (e.g., intra-chamber, intra-vascular, intra-pericardial, etc., which may be collectively referred to as "cardiac space"); and acquiring information (e.g., via one or more measured potentials) to determine a location, locations or displacement for at least one of the one or more electrodes using an electroanatomic mapping system (e.g., the ENSITE® NAVX® system or other system with appropriate features). In such a method, the positioned electrodes may be configured for acquisition of electrical information indicative of physiological function (e.g., IEGMs, muscle signals, nerve signals, etc.). Further, with respect to acquisition of information, an acquisition system may operate at an appropriate sampling rate. For example, an acquisition system for mechanical information may operate at a sampling rate of about 100 Hz (e.g., the ENSITE® NAVX® system can sample at about 93 Hz) and an acquisition system for electrical information may operate at a sampling rate of about 1200 Hz (e.g., in unipolar, bipolar or other polar arrangement).

As explained, the location information is used to map other information (see, e.g., the mapping of the block 330 of FIG. 3). In turn, a therapy may be selected or optimized or condition diagnosed based at least in part on one or more maps.

An exemplary method may include preparing a patient for both implant of a device such as the device 100 of FIGS. 1 and 2 and for electroanatomic mapping study. Such preparation may occur in a relatively standard manner for implant prep, and using the ENSITE® NAVX® system or other similar technology for the mapping prep. As described herein, any of a variety of electroanatomic mapping or locating systems that can locate indwelling electrodes in and around the heart may be used.

Once prepped, a clinician or robot may place leads and/or catheters in the patient's body, including any leads to be chronically implanted as part of a therapy system (e.g., CRT), as well as optional additional electrodes that may yield additional information (e.g., to increase accuracy by providing global information or other information).

After an initial placement of an electrode-bearing catheter or an electrode-bearing lead, a clinician may then connect one or more electrodes to an electroanatomic mapping or locating system. The term "connection" can refer to physical electrical connection or wireless connection (e.g., telemetric, RF, ultrasound, etc.) with the electrodes or wireless connection with another device that is in electrical contact with the electrodes.

Once an appropriate connection or connections have been made, real-time position data for one or more electrodes may be acquired for various configurations or conditions. For example, position data may be acquired during normal sinus rhythm; pacing in one or more chambers; advancing, withdrawing, or moving a location of an electrode; pacing one or more different electrode configurations (e.g. multisite pacing); or varying inter-stimulus timing (e.g. AV delay, VV delay).

In various examples, simultaneous to the position recording, an intracardiac electrogram (IEGM) from each electrode can also be recorded and associated with the anatomic position of the electrode. While various examples refer to simultaneous acquisition, acquisition of electrical information and acquisition of location information may occur sequentially (e.g., alternate cardiac cycles) or interleaved (e.g., both acquired during the same cardiac cycle but offset by sampling time or sampling frequency).

In various exemplary methods, electrodes within the cardiac space may be optionally positioned at various locations (e.g., by continuous movement or by discrete, sequential moves), with a mapping system recording the real-time position information at each electrode position in a point-by-point manner. Such position data can by associated with a respective anatomic point from which it was collected. By moving the electrodes from point to point during an intervention, the position data from each location can be incorporated into a single map, model, or parameter.

As explained, an exemplary method may include mapping one or more parameters. In turn, an algorithm or a clinician may select a configuration (e.g., electrode location, multisite arrangement, AV/VV timing) that yielded the best value for an electromechanical delay parameter and use the selected configuration as a chronic configuration for the CRT system. Such a chronic configuration may be optionally updated from time to time (e.g., during a follow-up visit, in a patient environment, etc., depending on specific capabilities of a system).

Various exemplary methods, using either a single parameter or a combination of more than one parameter, may automatically select a configuration, present an optimal configuration for acknowledgement by a clinician, or present various configurations to a clinician along with pros and cons of each configuration (e.g., in objective or subjective terms). For example, a particular configuration may be associated with a high power usage that may excessively drain a power source of an implantable device (e.g., device battery 276). Other pros and cons may pertain to patient comfort (e.g., pain, lack of pain, overall feeling, etc.).

An exemplary method may rely on certain equipment at time of implant or exploration and other equipment after implantation of a device to deliver a cardiac therapy. For example, during an intraoperative procedure, wireless communication may not be required; whereas, during a follow-up visit, measured potentials for position of chronically implanted electrodes (e.g., mechanical information) and of measured IEGMs using chronically implanted electrodes (e.g., electrical information) may be communicated wirelessly from an implanted device to an external device. With respect to optimization of a chronically implanted system, in general, electrode location will not be altered (e.g., except for dislocation or failure), but other parameters altered to result in an optimal configuration (e.g., single- or multi-site arrangement, polarity, stimulation energy, timing parameters, etc.).

As discussed herein, various exemplary techniques deliver current and measure potential where potential varies typically with respect to cardiac mechanics (e.g., due to motion). For example, electrodes for delivery of current may be placed at locations that do not vary significantly with respect to cardiac mechanics or other patient motion (e.g., breathing) while one or more electrodes for measuring potential may be placed at a location or locations that vary with respect to cardiac mechanics or other patient motion. Alternatively, electrodes for measuring potential may be placed at locations that do not vary significantly with respect to cardiac mechanics or other patient motion while one or more electrodes for delivery of current may be placed at a location or locations that vary with respect to cardiac mechanics or other patient motion. Various combinations of the foregoing arrangements are possible as well. Electrodes may be associated with a catheter or a lead. In some instances, an electrode may be a "stand-alone" electrode, such as a case electrode of an implantable device (see, e.g., the case electrode 200 of the device 100 of FIGS. 1 and 2).

Figure 5:
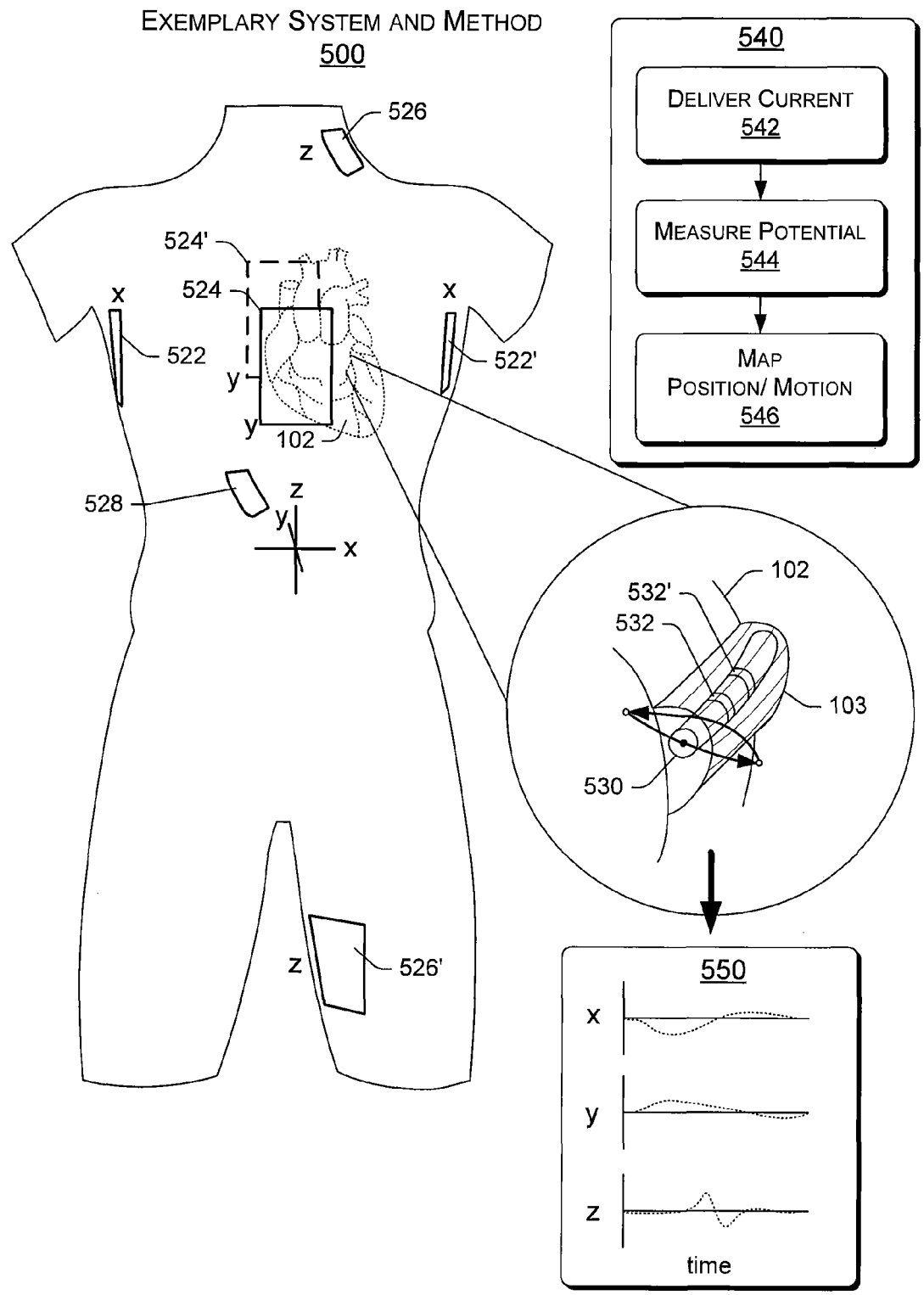
FIG. 5 is an exemplary arrangement of a lead and electrodes for acquiring localized information and optionally other information.

FIG. 5 shows an arrangement and method 500 that may rely in part on a commercially available system marketed as ENSITE® NAVX® navigation and visualization system (see also LocaLisa system). The ENSITE® NAVX® system is a computerized storage and display system for use in electrophysiology studies of the human heart. The system consists of a console workstation, patient interface unit, and an electrophysiology mapping catheter and/or surface electrode kit. By visualizing the global activation pattern seen on color-coded isopotential maps in the system, in conjunction with the reconstructed electrograms, an electrophysiologist can identify the source of an arrhythmia and can navigate to a defined area for therapy. The ENSITE® system is also useful in treating patients with simpler arrhythmias by providing non-fluoroscopic navigation and visualization of conventional electrophysiology (EP) catheters.

As shown in FIG. 5, electrodes 532, 532', which may be part of a standard EP catheter 530 (or lead), sense electrical potential associated with current signals transmitted between three pairs of surface electrode patches 522, 522' (x-axis), 524, 524' (y-axis) and 526, 526' (z-axis). An addition electrode patch 528 is available for reference, grounding or other function. The ENSITE® NAVX® System can also collect electrical data from a catheter and can plot a cardiac electrogram from a particular location (e.g., cardiac vein 103 of heart 102). Information acquired may be displayed as a 3-D isopotential map and as virtual electrograms. Repositioning of the catheter allows for plotting of cardiac electrograms from other locations. Multiple catheters may be used as well. A cardiac electrogram or electrocardiogram (ECG) of normal heart activity (e.g., polarization, depolarization, etc.) typically shows atrial depolarization as a "P wave", ventricular depolarization as an "R wave", or QRS complex, and repolarization as a "T wave". The ENSITE® NAVX® system may use electrical information to track or navigate movement and construct three-dimensional (3-D) models of a chamber of the heart.

A clinician can use the ENSITE® NAVX® system to create a 3-D model of a chamber in the heart for purposes of treating arrhythmia (e.g., treatment via tissue ablation). To create the 3-D model, the clinician applies surface patches to the body. The ENSITE® NAVX® system transmits an electrical signal between the patches and the system then senses the electrical signal using one or more catheters positioned in the body. The clinician may sweep a catheter with electrodes across a chamber of the heart to outline structure. Signals acquired during the sweep, associated with various positions, can then be used to generate a 3-D model. A display can display a diagram of heart morphology, which, in turn, may help guide an ablation catheter to a point for tissue ablation.

With respect to the foregoing discussion of current delivery and potential measurement, per a method 540, a system (e.g., such as the ENSITE® NAVX® system) delivers low level separable currents from the three substantially orthogonal electrode pairs (522, 522', 524, 524', 526, 526') positioned on the body surface (delivery block 542). The specific position of a catheter (or lead) electrode within a chamber of the heart can then be established based on three resulting potentials measured between the recording electrode with respect to a reference electrode, as seen over the distance from each patch set to the recording tip electrode (measurement block 544). Sequential positioning of a catheter (or lead) at multiple sites along the endocardial surface of a specific chamber can establish that chamber's geometry, i.e., position mapping (position/motion mapping block 546). Where the catheter (or lead) 530 moves, the method 540 may also measure motion.

In addition to mapping at specific points, the ENSITE® NAVX® system provides for interpolation (mapping a smooth surface) onto which activation voltages and times can be registered. Around 50 points are required to establish a surface geometry and activation of a chamber at an appropriate resolution. The ENSITE® NAVX® system also permits the simultaneous display of multiple catheter electrode sites, and also reflects real-time motion of both ablation catheters and those positioned elsewhere in the heart.

The ENSITE® NAVX® system relies on catheters for temporary placement in the body. Various exemplary techniques described herein optionally use one or more electrodes for chronic implantation. Such electrodes may be associated with a lead, an implantable device, or other chronically implantable component. Referring again to FIG. 3, the configuration block 310 indicates that intraoperative configurations 312 and chronic configurations 314 may be available. Intraoperative configurations 312 may rely on a catheter and/or a lead suitable for chronic implantation.

With respect to motion (e.g., change in position with respect to time), the exemplary system and method 500 may track motion of an electrode in one or more dimensions. For example, a plot 550 of motion versus time for three dimensions corresponds to motion of one or more electrodes of the catheter (or lead) 530 positioned in a vessel 103 of the heart 102 where the catheter (or lead) 530 includes the one or more electrodes 532, 532'. Two arrows indicate possible motion of the catheter (or lead) 530 where hysteresis may occur over a cardiac cycle. For example, a systolic path may differ from a diastolic path. An exemplary method may analyze hysteresis for any of a variety of purposes including selection of a stimulation site, selection of a sensing site, diagnosis of cardiac condition, etc.

The exemplary method 540, as mentioned, includes the delivery block 542 for delivery of current, the measurement block 544 to measure potential in a field defined by the delivered current and the mapping block 546 to map position or motion based at least in part on the measured potential. According to such a method, position or motion during systole and/or diastole may be associated with electrical information. Alone, or in combination with electrical information, the position or motion information may be used for selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc.

The system 500 may use one or more features of the aforementioned ENSITE® NAVX® system. For example, one or more pairs of electrodes (522, 522', 524, 524', 526, 526' and optionally 528) may be used to define one or more dimensions by delivering an electrical signal or signals to a body and/or by sensing an electrical signal or signals. Such electrodes (e.g., patch electrodes) may be used in conjunction with one or more electrodes positioned in the body (e.g., the electrodes 532, 532').

The exemplary system 500 may be used to track position or motion of one or more electrodes due to systolic function, diastolic function, respiratory function, etc. Electrodes may be positioned along the endocardium and/or epicardium during a scouting or mapping process for use in conjunction with electrical information. Such information may also be used alone, or in conjunction with electrical information, for identifying the optimal location of an electrode or electrodes for use in delivering CRT. For example, a location may be selected for optimal stimulation, for optimal sensing, or other purposes (e.g., anchoring ability, etc.).

With respect to stimulation, stimulation may be delivered to control cardiac mechanics (e.g., contraction of a chamber of the heart) and position or motion information may be acquired where such information is associated with the controlled cardiac mechanics. An exemplary selection process may identify the best stimulation site based on factors such as electrical activity, electromechanical delay, extent of motion, synchronicity of motion where motion may be classified as motion due to systolic function or motion due to diastolic function. In general, motion information corresponds to motion of an electrode or electrodes (e.g., endocardial electrodes, epicardial electrodes, etc.) and may be related to motion of the heart or other physiology.

Figure 6:
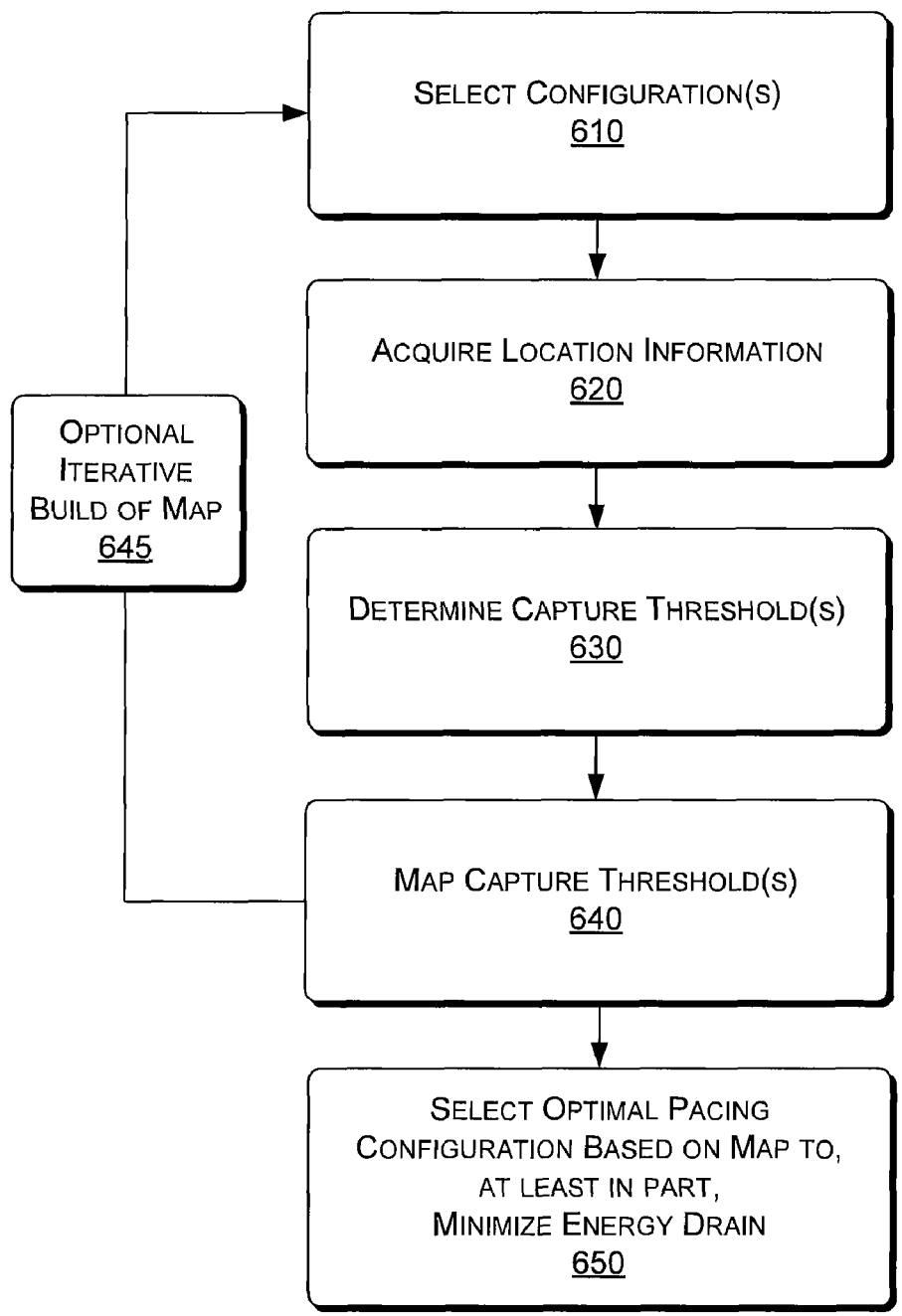
FIG. 6 is a block diagram of an exemplary method for acquiring location information and capture thresholds and mapping the capture thresholds based at least in part on the location information.

FIG. 6 shows an exemplary method 600 that includes mapping capture thresholds for selecting an optimal pacing configuration. The method 600 commence in a selection block 610 that selects one or more configurations to be tested. In general, such configurations include a variety of different electrode locations, combinations of electrodes or the like where location information can be associated with capture threshold information to generate a map. In an acquisition block 620, a localization system acquires location information for one or more selected configurations (e.g., based on sensed potentials in a current field or fields). A determination block 630 follows that determines a capture threshold for each of the one or more selected configurations. A map block 640 maps the capture threshold or thresholds based on the acquired location information. As indicated by an optional loop labeled 645, the method 600 may optionally proceed in an iterative manner when building a map. For example, the map block 640 may update a displayed map while additional data is collected and analyzed.

The map block 640 may generate localized capture threshold data for rendering a capture threshold map in conjunction with anatomical features or markers. Such data may be rendered by a computing device (e.g., via one or more graphics processing units) to a display. In turn, a clinician can view a displayed map to select an optimal pacing configuration per a selection block 650.

As described herein, the displayed map may show locations where a capture threshold or capture thresholds are low and therefore minimize current drain of a pacing therapy that relies on an implantable device with a limited power supply. With respect to such a selection, a clinician may account for one or more other factors germane to therapy. For example, a particular location may provide a low capture threshold and hence a reduced energy drain, however, the location may be sub-optimal for reduction of ventricular dyssynchrony, sensing IEGMs, avoiding undesirable nerve stimulation, etc. As described herein, such therapy factors may be accounted for by displaying a composite map or by displaying multiple maps (e.g., adjacent to each other on a display for ease of comparison).

Referring again to the determination block 630 of the method 600, capture thresholds may be determined in any of a variety of manners. A particular algorithm for determining a capture threshold is known as the AUTOCAPTURE™ algorithm (St Jude Medical, Inc., Cardiac Rhythm Management Division, Sylmar, Calif.), which can automatically monitor capture on a beat-by-beat basis, provide a high output back-up pulse in the setting of loss of capture associated with the primary output pulse and adjust output and/or assess capture threshold on both a scheduled and on an as-needed basis. In general, such algorithms place patient safety ahead of battery current drain; however, when the chronic threshold is low, this algorithm also minimizes battery current drain, effectively increasing device longevity.

As conventionally programmed, the AUTOCAPTURE™ algorithm runs a capture threshold assessment test once every eight hours. To perform this test, paced and sensed AV delays are temporarily shortened to about 50 ms and to about 25 ms, respectively. The AUTOCAPTURE™ algorithm generally uses a bottom-up approach (also referred to as an "up threshold") and a back-up pulse for safety when an output pulse does not result in capture. With respect to use of a back-up pulse, an output pulse of about 4.5 volts is typically sufficient to achieve capture where lead integrity is not an issue. Use of a back-up pulse may also adequately benefit certain patients that are quite sensitive to loss of capture. For example, patients having a high grade AV block may be sensitive to protracted asystole. Even if loss of capture is recognized immediately and adjustment is completed in less than about 1 second, a patient may still have been asystolic for over 2 seconds utilizing a standard capture threshold test. A back-up pulse typically prevents occurrence of such a long asystolic period.

With respect to detection of an evoked response (ER), various exemplary methods use a unipolar primary pulse configuration with a bipolar ER detection configuration, a unipolar primary pulse configuration with a unipolar ER detection configuration, a bipolar primary pulse configuration with a bipolar ER detection configuration, a bipolar primary pulse configuration with a unipolar ER detection configuration and/or no primary pulse ER detection. As described herein, such configurations can be assessed, localized and mapped to aid in optimization of therapy.

At implant or thereafter, a clinician may perform a threshold test to determine if an algorithm for capture is working properly and for further assessment. In systems that use the AUTOCAPUTRE™ algorithm, a clinical test can include temporarily setting PV delay and AV delay intervals to about 25 ms and about 50 ms, respectively. Shortening of the AV and PV delays acts to minimize risk of fusion. Fusion may compromise measurement and detection of an ER signal, especially ER signal amplitude. If results from the follow-up test indicate that enabling of the algorithm would not be safe due to too low an evoked response or too high a polarization signal, then the algorithm may be disabled and a particular, constant output programmed to achieve capture with a suitable safety margin. If the ER and polarization signals are appropriate to allow an autocapture algorithm to be enabled, an ER sensitivity will typically be recommended by a clinician or programmer and may then be programmed as it relates to detection of an ER signal.

Clinical tests for the AUTOCAPTURE™ algorithm typically work top down. If loss of capture occurs, a first output adjustment step typically sets a high output and then decreases output by about 0.25 volts until loss of capture occurs (also referred to as a "down threshold"). At this point, output is increased in steps of a lesser amount (e.g., about 0.125 volts) until capture occurs. Once capture occurs, a working or functional margin of about 0.25 volts is added to the capture threshold output value. Hence, the final output value used is the capture threshold plus a working margin. Systems that use a fixed output use a safety margin ratio instead of an absolute added amount. The safety margin is a multiple of the measured capture threshold, commonly 2:1 or 100% to allow for fluctuations in the capture threshold between detailed evaluations at the time of office visits.

With respect to a down threshold approach, in instances where loss of capture occurs, a first output adjustment step typically increases output until capture is restored. Steps used in the AUTOCAPTURE™ algorithm are typically finer than those used in an intraoperative or routine follow-up capture threshold test. At times, a down threshold algorithm may result in a threshold that is as much as 1 volt lower from the result of an up threshold algorithm. This has been termed a Wedensky effect. In general, an actual output setting (e.g., including safety margin) may be adjusted to account for whether a patient is pacemaker dependent. In a patient who is not dependent on the pacing system, a narrower safety margin may be selected than would be the case for a patient whom the physician considers to be pacemaker dependent.

After implant, some positional instability may occur along with a normal marked inflammatory reaction at the electrode-tissue interface (e.g., "lead maturation"). Hence, while an intraoperative procedure may reliably map capture thresholds, actual chronic capture thresholds can be expected to change due to lead maturation or other factors. However, a capture threshold map generated based on acute (intraoperative) information may nevertheless serve as a foundation for selecting an initial or subsequent configuration. Further, where positional instability issues or other lead failure issues (e.g., mechanical degradation, etc.) arise, such capture threshold map may be relied on, at least in part, in providing a remedy. For example, if another lead continues to function, then a previously generated map may be consulted as to suitable configurations that rely on the other lead.

As mentioned, energy drain may be mapped or an important parameter associated with energy drain may be mapped. As most implantable cardiac therapy devices have a limited power supply, energy drain is often a factor when selecting a chronic configuration or configurations. Energy drain of an implantable device is determined in part by aspects of operation (e.g., maintenance operations, sensing operations, pacing operations, shock operations, specialized algorithms, etc.) and in part by component characteristics, the body and component/body interactions.

With respect to components and component/body interactions, consider that high electrode impedance reduces current flowing through an electrode. In general, lead impedance for a given electrode is not programmable as it is usually a characteristic of the electrode. Impedance typically increases as overall diameter of an electrode decreases; however, a decrease in diameter acts to increase polarization. Polarization can be reduced by increasing electrode surface area, for example, by an appropriate surface texture. Excessive polarization also is detrimental for sensing, especially sensing cardiac electrical signals of an evoked response (e.g., as in a capture detection algorithm). To address polarization, some algorithms apply energy to "counteract" post-pulse polarization. As such algorithms expend energy, they affect energy drain.

For pacing or shocking, impedance may be considered a sum of all forces opposing flow of current in an electrical circuit. Lead impedance for a conventional pacing lead generally falls into a range of about 300 to 1500 Ω. So-called high impedance leads or electrodes may have impedance in excess of 1500 Ω. In a scenario where an electrode impedance exceeds 2500 Ω, current drain from an associated and typical cardiac stimulation device is minimal and less than 10 µA. While such a scenario is often associated with undesirable conditions (e.g., lead failure), the battery life would be quite long, for example, equal to or greater than 10 years. Thus, a scenario that involves a fractured wire, a loose connection, and/or no connection may be associated with a low current drain and high impedance; noting that various scenarios may also result in ineffective stimuli, inappropriate stimuli, faulty sensing, etc.

In a second scenario representative of normal operation, an electrode impedance of approximately 500 Ω (e.g., a pacing electrode), an average current drain of approximate 21 µA and a battery life of about 5 years may be expected. In general, normal impedance ranges from about 300 Ω to about 1500 Ω for cardiac pacing electrodes. In a third scenario where electrode impedance is less than about 200 Ω, an average current drain of about 63 µA and a shortened battery life of about 2 years may result. Such a scenario is undesirable for at least several reasons. First, the increase in current drain can shorten battery life dramatically and, second, an insulation break typically exposes at least a portion of a lead conductor and thus creates secondary current paths. As described herein, in an intraoperative environment, leads are typically in good condition and actual current drain depends on electrode location, pacing voltage, therapy, etc.

As mentioned, various capture algorithms rely on sensing cardiac electrical signals to detect evoked responses. Sensing or detection can rely on so-called "sensitivity", which is a threshold that may vary based on a variety of factors. In essence, a sensitivity threshold acts to filter out electrical signals below the threshold. Hence, such an approach can filter out low-level noise and only respond to, or analyze, signals that, for example, have amplitudes above the sensitivity threshold.

In various capture algorithms, if a capture detection feature makes an initial determination of non-capture, then an auto sensitivity feature is implemented. For example, after an initial determination of non-capture, an auto sensitivity algorithm can lower a sensitivity threshold (to thereby increase sensitivity) and repeat a capture assessment using the lower threshold to decide if capture actually occurred but the sensitivity threshold was too high (sensitivity too low) or to confirm that capture did not occur.

Sensing and detection typically account for various factors to make detection more accurate. For example, a sense refractory period (SRP), which is an interval or timing cycle following a sensed or paced event during which a sense amplifier senses but does not allow a response (e.g., delivery of a stimulus, reset of a timing cycle, etc.) to sensed information may be implemented. As another example, consider use of a blanking period that temporarily disables a sense amplifier whereby the sense amplifier will not respond at all to incoming signals.

In a particular example, a sense refractory period (SRP) commences at a time associated with detection of a cardiac event. In this example, the SRP terminates by timing out or by inactivity (no additional detected events). In this example, during the SRP, sensitivity can be set to the maximum sensitivity, which corresponds to a smaller sensitivity threshold value (e.g., a low potential value in mV to allow for detection of low amplitude events).

According to such schemes, an increase in sensitivity means that smaller signals can be detected. Sensitivity is typically programmed in terms of the amplitude of the smallest signal that can be detected. Hence, a 1 mV sensitivity setting is a higher sensitivity than a 2 mV setting. At a 1 mV setting, a sensing system is more sensitive when compared to a 2 mV setting. By the same token, where less sensitivity or decreased sensitivity is desired, a programmable sensitivity is typically programmed to a higher potential value (e.g., a higher value in mV, etc.). A sensitivity algorithm may implement a decay delay (DD), which acts to maintain a sensitivity threshold value for a period of time and then decay thereafter (e.g., to increase sensitivity). Such an approach can during the delay avoid sensing of T waves and other known but inappropriate low amplitude signals that may otherwise be sensed at a very sensitive setting.

As described herein, for a sensitivity algorithm, decay delay, slope of decay and/or other sensitivity parameter(s) are optionally set based, at least in part, on an R-T interval. An exemplary method can acquire location information and R-T intervals and generate a map of R-T intervals to aid in programming such sensitivity parameters.

Figure 7:
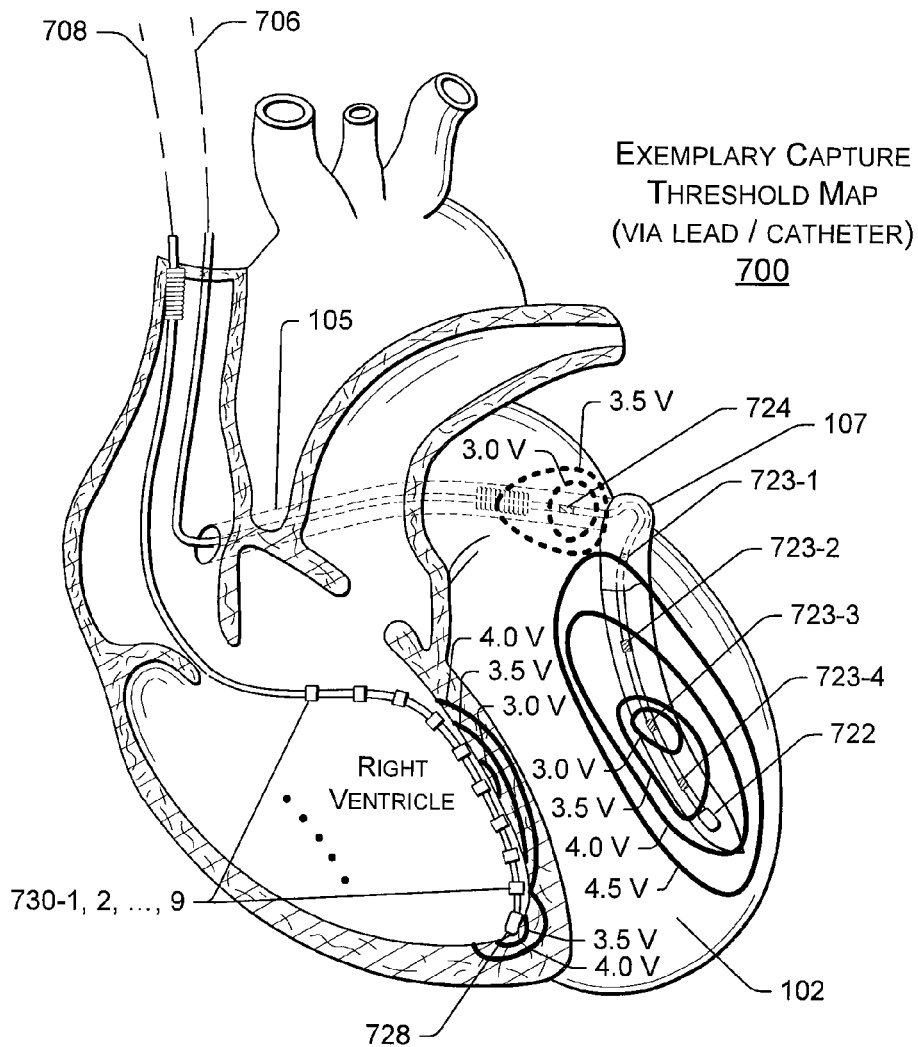
FIG. 7 is a diagram of an exemplary capture threshold map and associated plots of capture thresholds versus electrode position or number.
Figure 7:
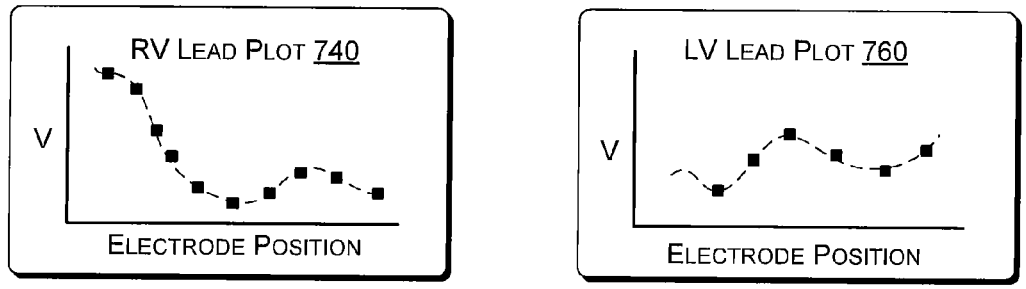

FIG. 7 shows an exemplary capture threshold map 700. In the example of FIG. 7, the map 700 is shown with respect to a diagram of the heart 102 that also shows positions of a left ventricular lead 706 and a right ventricular lead 708. As described herein, the map 700 can be based on information acquired using one or more catheters, one or more leads or a combination of one or more catheters and one or more leads. For example, a clinician may maneuver an electrode-bearing catheter through various chambers and vessels of the heart 102 and perform capture threshold tests at various locations where a localization system records the locations. In turn, a mapping application can map the capture threshold data with respect to the locations. As shown in the example of FIG. 7, the map 700 includes contours for a variety of capture threshold voltages ranging from 3.0 V to 4.5 V.

A mapping application may be programmed to allow a clinician to display a selected range of capture thresholds over one or more selected regions of the heart. For example, for the map 700, a clinician may have entered a range of 3.0 V to 4.5 V and specified a septal wall region, a vein region suitable for LV pacing and a coronary sinus region suitable for LA pacing or shocking. Given such specifications, the mapping application generates a map with contours or other markers to indicate where the range of capture thresholds exists for the different regions. For the map 700 of FIG. 7, contours are shown for these three regions where the dashed contour lines correspond to the coronary sinus region. In the example of FIG. 7, the left ventricular lead 706 includes a coronary sinus electrode 724, a series of electrodes 723 (e.g., 723-1 to 723-4)

and a tip electrode 722 while the right ventricular lead 706 includes a series of electrodes 730 (e.g., 730-1 to 730-9) and a tip electrode 728.

Based on the map 700, the electrode 723-3 corresponds to a left ventricular region with a low capture threshold (i.e., about 3.0 V). Regardless of whether the map 700 was generated using a unipolar, bipolar or other multipolar electrode configuration, it still provides a clinician with useful information sufficient to narrow possible chronic electrode configuration choices from many to a few. Thus, the electrode 723-3 may be selected for delivery of pacing energy in a unipolar, bipolar (e.g., optionally with a neighboring electrode in a low capture threshold region) or other multipolar electrode configuration with some assurance that the capture threshold will be lower than configurations that do not use the electrode 723-3.

Based on the map 700, the electrode 730-6 corresponds to a septal wall region (e.g., for right ventricular, left ventricular or bi-ventricular pacing) with a low capture threshold (i.e., about 3.0 V). A clinician may rely on such information to select the electrode 730-6 for use in a unipolar, bipolar or other multipolar electrode configuration for pacing the heart.

Based on the map 700, the electrode 724 corresponds to a coronary sinus region (e.g., for left atrial, left ventricular or bi-ventricular pacing) with a low capture threshold (i.e., about 3.0 V). A clinician may rely on such information to stimulate the left atrium, for example, where an atrial arrhythmia occurs with a left atrial rotor that may be terminated using anti-tachycardia pacing (ATP) or other anti-tachycardia therapy delivered using the electrode 724.

As described herein, given the map 700, a clinician may maneuver the lead 706 into the coronary sinus 105 and a tributary vessel 107 of the coronary sinus 105 and maneuver the lead 708 into the right ventricle to align with favorable capture threshold contours. In turn, electrode positions for the leads may be located and correlated with the mapped capture threshold contours to generate a plot 740 for the RV lead 708 and a plot 760 for the LV lead 706. The plots 740, 760 readily show minimum and maximum capture thresholds for specific lead electrodes based on the location of the lead electrodes (e.g., as acquired using a localization system).

In combination, the map 700 and the plots 740, 760 allow a clinician to readily determine which electrodes may be used for delivery of pacing energy to low capture threshold portions of the heart 102. Further, the clinician may determine a ranking of electrodes should a selected electrode be unsuitable due to one or more other factors (e.g., sub-optimal synchrony, sub-optimal sensing, etc.). Yet further, the map 700 and plots 740, 760 may be stored or archived and used during patient consultation or analysis (e.g., during a follow-up visit that occurs after implantation of the leads 706, 708). For example, if one of the leads 706, 708 fails the map 700 may assist a clinician in reprogramming an implanted device to delivery pacing energy using the other lead.

As described herein, an exemplary method includes selecting an electrode configuration for delivery of cardiac pacing stimuli where the electrode configuration includes at least one in vivo electrode (i.e., positioned within a patient's body); acquiring location information for one or more of the at least one in vivo electrode of the selected electrode configuration; determining a capture threshold value responsive to delivering cardiac pacing stimuli using the selected electrode configuration; selecting another electrode configuration for delivery of cardiac pacing stimuli where the electrode configuration includes at least one in vivo electrode; acquiring location information for one or more of the at least one in vivo electrode of the selected other electrode configuration; determining a capture threshold value responsive to delivering cardiac pacing stimuli using the selected other electrode configuration; for the selected electrode configuration and the selected other electrode configuration, generating a map that maps the corresponding capture threshold values based on the acquired location information for the selected electrode configuration and the acquired location information for the selected other electrode configuration; and rendering the map and cardiac anatomical markers to a display to allow a user to observe a relationship between capture threshold and cardiac anatomy. For example, the map 700 of FIG. 7 shows capture threshold values and features of a heart that would allow a clinician to observe relationships between capture thresholds and cardiac location or anatomy (e.g., ventricular markers, atrial markers or ventricular markers and atrial markers). Such a map may be stored to a storage accessible by an implantable device programmer or other computing or display device.

An exemplary method can include selecting an electrode configuration for chronic delivery of a cardiac pacing therapy based at least in part on a rendered map and cardiac anatomical markers. An exemplary capture threshold method may also include determining current drain values based on the capture threshold values and generating a map that maps the current drain values based on acquired location information for a selected electrode configuration and acquired location information for another selected electrode configuration. In such a method, each current drain value may be based in part on an electrode impedance value for a given electrode configuration.

As described herein, an exemplary method can map data over time. For example, a method may, for one or more selected electrode configuration, include determining maturation compensated capture threshold values.

An exemplary system can include one or more processors; memory; and control logic configured to: select an electrode configuration for delivery of cardiac pacing stimuli where the electrode configuration includes at least one in vivo electrode; acquire location information for one or more of the at least one in vivo electrode of the selected electrode configuration; determine a capture threshold value responsive to delivering cardiac pacing stimuli using the selected electrode configuration; select another electrode configuration for delivery of cardiac pacing stimuli where the electrode configuration includes at least one in vivo electrode; acquire location information for one or more of the at least one in vivo electrode of the selected other electrode configuration; determine a capture threshold value responsive to delivering cardiac pacing stimuli using the selected other electrode configuration; for the selected electrode configuration and the selected other electrode configuration, generate a map that maps the corresponding capture threshold values based on the acquired location information for the selected electrode configuration and the acquired location information for the selected other electrode configuration; and render the map and cardiac anatomical markers to a display to allow a user to observe a relationship between capture threshold and cardiac anatomy. Such control logic may be stored as instructions on one or more computer-readable media (e.g., memory) and/or be implemented by one or more devices (e.g., an implanted device and an external device).

Figure 8:
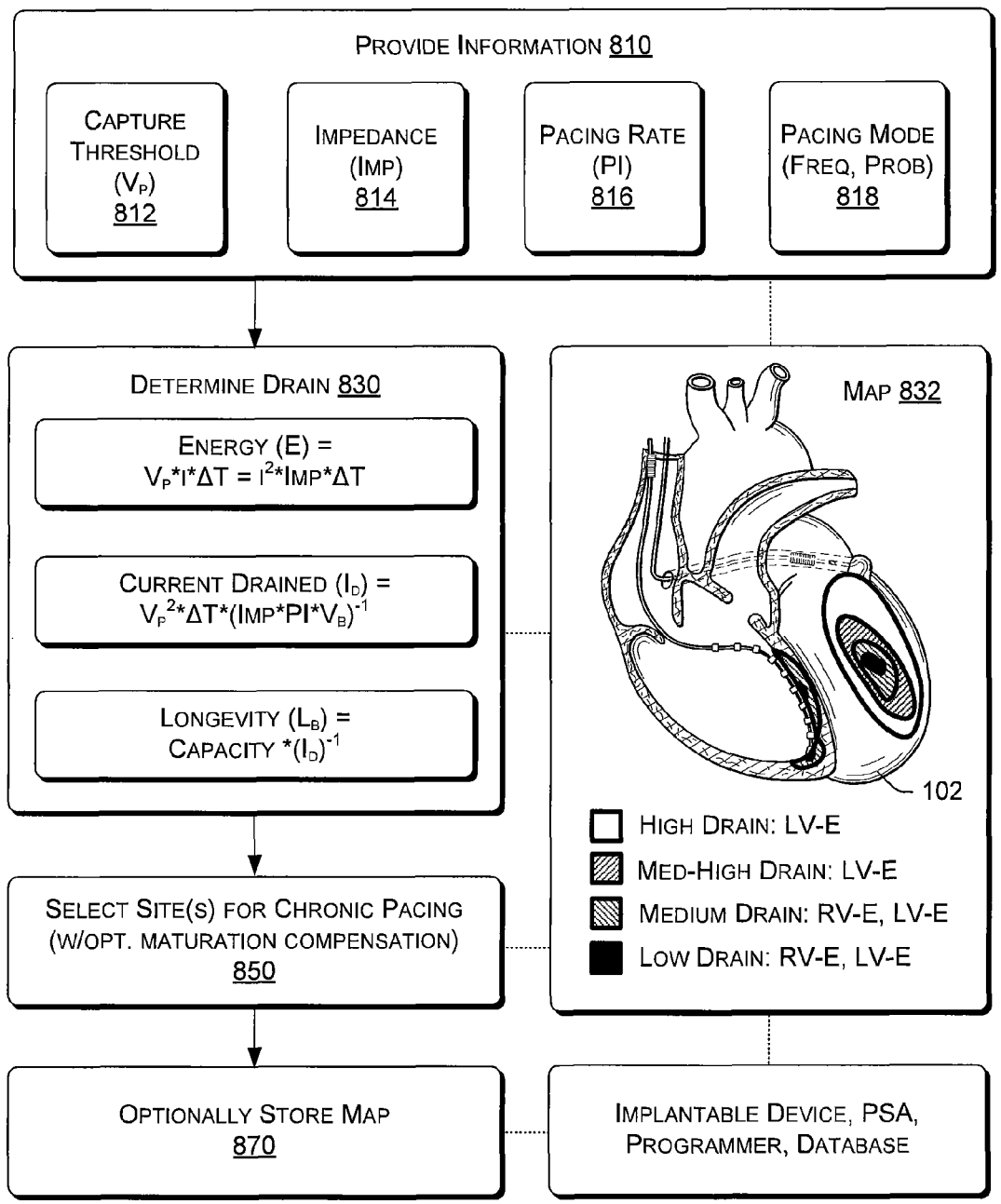
FIG. 8 is a block diagram of an exemplary method for optimizing energy drain of an implantable device that includes mapping drain with respect to anatomical features of a human heart.

FIG. 8 shows an exemplary optimization method 800 for reducing energy drain of an implantable device. The method 800 commences in a provision block 810 that provides or provides access to information. In the example of FIG. 8, the information includes capture threshold information 812, impedance information 814, pacing rate information 816 and pacing mode information 818. The provided information of block 810 may include less or more than the information shown, however, the provided information is typically sufficient to determine current drain. In general, parameters that influence longevity of an implantable power supply include pulse amplitude, pulse width, working mode and rates programmed, lead impedance and static energy drain. While adjustments of all of these parameters can influence longevity, conventionally, adjustments to pulse amplitude and to pulse width have significant impact on longevity.

As shown in FIG. 8, a determination block 830 relies on the provided information (e.g., 812, 814, 816, 818) to determine energy, current drain and longevity of a power supply of an implantable device. The determination block 830 may also account for energy associated with maintenance operations, shocking operations, etc.

As indicated by various dashed lines, the method 800 can include mapping or accessing a map 832. In the example of FIG. 8, the map 832 shows regions of the heart 102 along with contours as to energy or current drain. Such contours can be mapped based on drain determinations from the determination block 830. In the map 832, an open contour shows a high drain region as associated with LV electrodes; a lower left to upper right hatched contour shows a medium-high drain region as associated with LV electrodes; an upper left to lower right hatched contour shows a medium drain region as associated with RV electrodes and LV electrodes; and a solid, filled contour shows a low drain region as associated with RV electrodes and LV electrodes.

As described herein, the method 800 includes a selection block 850 that selects one or more sites for chronic pacing. The selection block 850 relies on drain determinations of the determination block 830 as presented in the map 832. Thus, a clinician may select a site for chronic pacing, in part, by viewing the map 832 and deciding which electrode or electrodes correspond to low drain contour regions.

An exemplary system optionally includes a touch screen that allows a clinician to select (e.g., using a finger or stylus) a displayed electrode marker on a map (such as the map 832) and to thereby select an electrode for use in pacing. In an alternative arrangement, a mouse or trackball may be used to align a pointer with a displayed electrode marker to thereby select an electrode for use in pacing. Where the system includes various teatures of a pacing system analyzer (PSA) or an implantable device programmer, the selection may automatically program an implantable device to use the selected electrode (or electrode configuration).

Referring again to FIG. 8, a storage block 870 of the method 800 can optionally store the map 832. The storage block 870 may store the map 832 (e.g., as localized energy/current drain data) to an implantable device, a PSA, a device programmer or a database. A stored map may be later used to assess patient condition, device condition, etc.

Figure 9:
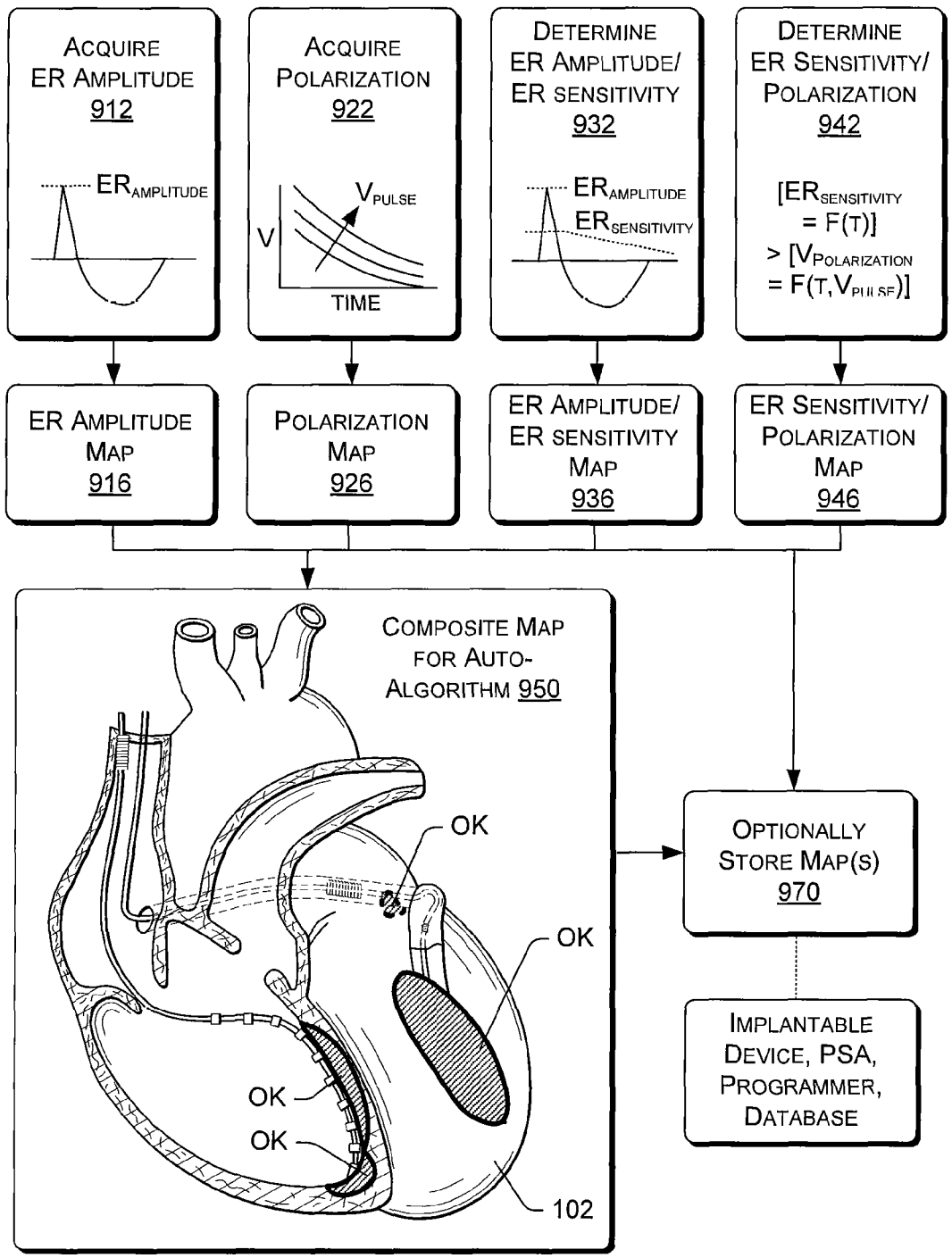
FIG. 9 is a block diagram of an exemplary method for mapping regions where certain qualification criteria are met for implanting a particular algorithm such as an automatic capture assessment algorithm.

As mentioned, a map may be used to decide whether a particular type of algorithm can be implemented. FIG. 9 shows an exemplary method 900 for qualification of an automatic algorithm such as the aforementioned AUTOCAPTURE™ algorithm. For example, to enable the AUTOCAPTURE™ algorithm, certain criteria may need to be met: ER amplitude >2.5 mV, polarization <4.5 mV, ER amplitude/ER sensitivity ratio >1.8:1 , and ER sensitivity/polarization ratio >1.7:1 . Such criteria are represented in the method 900 at an ER amplitude acquisition block 912, a polarization acquisition block 922, an ER amplitude/ER sensitivity ratio determination block 932, and an ER sensitivity/polarization ratio determination block 942. As described herein, the acquired information or determinations have associated location information as acquired by a localization system. The location information allows for mapping the acquired information or determinations with respect to cardiac anatomy.

In FIG. 9, each block includes some explanatory information such as a plot or an equation. The block 912 includes a plot of an evoked response where an ER amplitude is identified, the block 922 includes a plot of polarization versus time and pulse voltage, the block 932 includes a plot of an evoked response and ER sensitivity versus time and the block 942 includes an equation for ER sensitivity and polarization.

After acquisition of information, the method 900 enters a mapping phase where individual maps may be generated. For example, as shown in the example of FIG. 9, an ER amplitude map block 916 can generate an ER amplitude map, a polarization map block 926 can generate a polarization map, a ER amplitude/ER sensitivity map block 936 can generate a map of ER amplitude to ER sensitivity ratio, and a ER sensitivity/polarization map block 946 can generate a map of ER sensitivity to polarization ratio. The map blocks 916, 926, 936, 946 may include instructions for rendering a map to a display device or to store sufficient data in memory for use by a rendering algorithm (e.g., to memory associated with a graphics processer unit (GPU)).

To decide whether a particular algorithm qualifies for use (e.g., being enabled), in a composite map block 950, the method 900 generates a composite map (see, e.g., example map shown within the block 950). In the example of FIG. 9, the composite map indicates regions where the particular algorithm qualifies to optionally be enabled. Specifically, the composite map is shown with "OK" labels that identify four regions where the criteria are met. Given such a composite map, a clinician may narrow choices as to which electrodes may be used for pacing in conjunction with an automatic capture threshold assessment algorithm (e.g., the AUTOCAPTURE™ algorithm). In some instances, the choice may be narrowed to a single feasible electrode or electrode configuration for atrial pacing, right ventricular pacing, left ventricular pacing, etc.

As shown in FIG. 9, a storage block 970 optionally stores one or more of the maps (e.g., one or more individual maps, a composite map, etc.). The storage block 970 may store a map or maps (e.g., as localized data) to an implantable device, a PSA, a device programmer or a database. A stored map may be later used to assess patient condition, device condition, etc.

The previously described exemplary system with selection mechanisms (e.g., touch screen, mouse, etc.) may be used to associate electrodes and a particular algorithm to indicate whether an electrode can be used in conjunction with the particular algorithm. For example, in the composite map of FIG. 9, the clinician may disable an automatic capture threshold assessment algorithm for all electrodes that do not lie within or lie adjacent a qualifying region. Such a process may involve setting a character in a field of a data table of an implantable device (e.g., field "autocap": "0" disabled, "1" can be enabled). Once programmed in such a manner, during chronic operation, should a change in pacing configuration be required, the implanted device may access the data table to determine whether the automatic capture assessment algorithm can be enabled. While the predictive value of the stored information may change over time, it may still be used to avert testing or otherwise ensure patient safety and optionally device longevity (e.g., by only selecting from electrode configurations that can enable the automatic capture threshold assessment algorithm).

As described herein, an exemplary method includes, for each of a plurality of sensing configurations, acquiring an evoked response amplitude caused by delivery of a cardiac pacing stimulus; for each of the plurality of sensing configurations, acquiring a polarization amplitude caused by delivery of a cardiac pacing stimulus; for each of the plurality of sensing configurations, acquiring location information sufficient to locate, in three-dimensions, at least one sensing electrode; generating a map that maps the acquired evoked response amplitudes and the acquired polarization amplitudes based on the acquired location information; and rendering the map and cardiac anatomical markers to a display to allow a user to observe a relationship between the evoked response amplitude and the polarization amplitudes and cardiac anatomy. Such a method can include, based on the rendered map and cardiac anatomical markers, deciding whether a sensing configuration allows for enabling an algorithm of an implantable cardiac pacing device. For example, an algorithm may be an automatic capture threshold assessment algorithm that specifies a ratio between evoked response amplitude and polarization amplitude as an operational criterion.

An exemplary method can include selecting a sensing configuration, for sensing evoked responses during chronic delivery of a cardiac pacing therapy, based at least in part on a rendered map and cardiac anatomical markers. For example, such a method may include rendering one or more contours to a display where the one or more contours include a qualification contour that indicates whether a qualification criterion or criteria of an algorithm of an implantable cardiac pacing device are met. A method may further include programming an implantable cardiac therapy device to prohibit enabling an algorithm for one or more sensing configurations or to permit enabling an algorithm for one or more sensing configurations.

An exemplary system may include one or more processors; memory; and control logic configured to: for each of a plurality of sensing configurations, acquire an evoked response amplitude caused by delivery of a cardiac pacing stimulus; for each of the plurality of sensing configurations, acquire a polarization amplitude caused by delivery of a cardiac pacing stimulus; for each of the plurality of sensing configurations, acquire location information sufficient to locate, in three-dimensions, at least one sensing electrode; generate a map that maps the acquired evoked response amplitudes and the acquired polarization amplitudes based on the acquired location information; and render the map and cardiac anatomical markers to a display to allow a user to observe a relationship between the evoked response amplitude and the polarization amplitudes and cardiac anatomy. Such control logic may be stored as instructions on one or more computer-readable media (e.g., memory) and/or be implemented by one or more devices (e.g., an implanted device and an external device).

Figure 10:
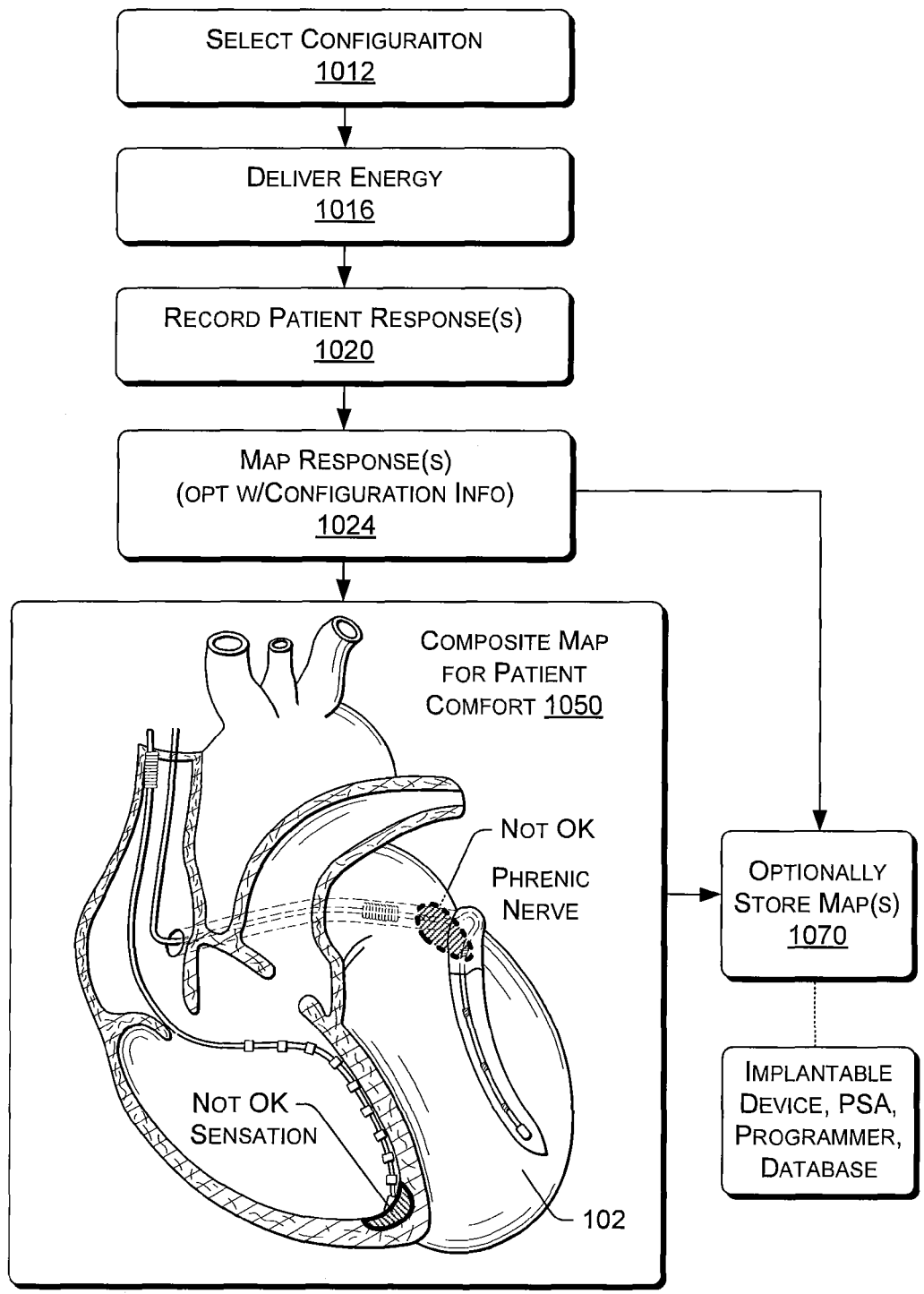
FIG. 10 is a block diagram of an exemplary method for mapping one or more undesirable effects of cardiac pacing such as phrenic nerve stimulation or patient discomfort.

As mentioned, various techniques can account for undesirable effects of pacing. For example, FIG. 10 shows an exemplary method 1000 that can account for patient discomfort or undesirable nerve stimulation that may occur during delivery of a pacing therapy using an implantable device such as the device 100 of FIGS. 1 and 2.

As to discomfort, pacing may cause some discomfort by various mechanisms. For example, pacing energy can affect sensory nerves. In general, there are three types of sensory afferent fibers that send sensory information to the central nervous system; unmyelinated C fibers send a long lasting delayed painful sensation, thinly myelinated Aδ fibers send a short and fast painful sensation and the thickly myelinated Aβ fibers send tactile information. If a particular electrode configuration stimulates such nerves, a patient may find that configuration discomforting.

As to nerve stimulation, undesirable phrenic nerve stimulation However, in some instance phrenic nerve stimulation can be desirable, for example, where a high energy pulse aims to stimulate the phrenic nerve during periods of apnea (e.g., sleep apnea). The phrenic nerve is made up mostly of motor nerve fibres for producing contractions of the diaphragm. In addition, it provides sensory innervation for various components of the mediastinum and pleura, as well as the upper abdomen (e.g., liver and gall bladder). The right phrenic nerve passes over the brachiocephalic artery, posterior to the subclavian vein, and then crosses the root of the right lung anteriorly and then leaves the thorax by passing through the vena cava hiatus opening in the diaphragm at the level of T8 . More specifically, with respect to the heart, the right phrenic nerve passes over the right atrium while the left phrenic nerve passes over the pericardium of the left ventricle and pierces the diaphragm separately.

The method 1000 commences in a selection block 1012 for selection of a configuration (see, e.g., the selection block 310 of the method 300 of FIG. 3). As described herein, the selected configuration includes one or more electrodes that are localized using a localization system. Corresponding location information may be acquired prior to selection or after selection to allow for generating a map of pacing effect or effects.

In the example of FIG. 10, a delivery block 1016 follows the selection block 1012 where the delivery block 1016 delivers energy relying on or according to the selected configuration. For example, the delivery block 1016 may use a selected electrode configuration to deliver energy at a pre-set upper level that could be experienced during a chronic pacing therapy or, in another example, the delivery block 1016 may select a configuration that specifies an energy level for delivery using a pre-set electrode configuration.

In a recordation block 1020, upon delivery of the energy or shortly thereafter, information is recorded via one or more sensors, observations or patient responses. For example, if phrenic nerve stimulation is a concern, an accelerometer (whether implanted or external) may register acceleration due to contraction of the diaphragm. In another example, a clinician may simply observe the patient to see if the delivered energy caused the diaphragm to contract. In yet another example, a patient may have a handheld device with an actuator to be actuated when the patient experiences discomfort and to record actuation events or to issue a signal responsive to actuation events.

In a map block 1024, the method 1000 relies on the recorded patient response or responses (which may be a sensed physiological response or responses that are noted regardless of whether a patient is conscious or not) to generate a map 1050 that maps one or more configuration parameters with the response or responses. In the example of FIG. 10, the map 1050 is a composite map that indicates a region associated with undesirable phrenic nerve stimulation and a region associated with patient sensation or discomfort. While the phrenic nerve stimulation region is shown on the posterior side of the heart 102, phrenic nerve stimulation may occur in any of a variety of regions and may depend on factors such as polarity (e.g., unipolar pacing using a can electrode).

The method 1000 further includes a storage block 1070 that optionally stores one or more maps (e.g., one or more individual maps, a composite map, etc.). The storage block 1070 may store a map or maps (e.g., as localized data) to an implantable device, a PSA, a device programmer or a database. A stored map may be later used to assess patient condition, device condition, etc.

The previously described exemplary system with selection mechanisms (e.g., touch screen, mouse, etc.) may be used to associate electrodes and desirable or undesirable aspects of a particular configuration. For example, a clinician may use a selection mechanism to select an electrode in a region associated with undesirable phrenic nerve stimulation. The system may be configured to store such an association in a data table (e.g., field "pns": "0" OK; "1" not OK). Such a data table may be stored in an implantable device such that electrodes with "1" in the "pns" data field are not used for delivery of cardiac pacing stimuli. Alternatively, association data may be stored in a database accessible by an implantable device programmer such that during a follow-up visit a clinician can access the data for the patient and avoid, as appropriate, programming the implanted device to delivery cardiac pacing stimuli using an electrode having a "1" in a "pns" data field.

According to the exemplary method 1000, a variety of responses may be recorded and mapped. Such responses may be noted by one or more sensors, one or more observations and/or one or more conscious patient responses. An exemplary system includes an actuator for actuation by a patient to indicate a level of discomfort or concern associated with delivery of energy using a selected localized configuration. Such an actuator may include levels from low to high (or other characterization). For example, using one selected configuration, a patient may use the actuator to indicate little discomfort at a level of 1 on a scale of 1 to 5 while using a different selected configuration, the patient may use the actuator to indicate significant discomfort at a level of 5 on the scale of 1 to 5. In turn, this information may be mapped with contours or other markers based at least in part on the location information for the two selected configurations.

As described herein, a mapping application may include a standard routine for generating contours based on discrete data points. Such a routine may account for the multi-dimensional nature of location data for a configuration. Such a routine may further have a preprogrammed and optionally scalable graphical model of a human heart. Correspondingly, anatomical cardiac markers (or outlines, graphics, etc.) may be scaled and displayed with contours or contours may be scaled and displayed with anatomical cardiac markers that may be fixed in some manner.

As described herein, an exemplary method includes: selecting an electrode configuration for delivery of cardiac pacing stimuli where the electrode configuration includes at least one in vivo electrode; acquiring location information for one or more of the at least one in vivo electrode of the selected electrode configuration; determining whether a phrenic nerve capture occurred responsive to delivering cardiac pacing stimuli using the selected electrode configuration; selecting another electrode configuration for delivery of cardiac pacing stimuli where the electrode configuration includes at least one in vivo electrode; acquiring location information for one or more of the at least one in vivo electrode of the selected other electrode configuration; determining whether phrenic nerve capture occurred responsive to delivering cardiac pacing stimuli using the selected other electrode configuration; for the selected electrode configuration and the selected other electrode configuration, generating a map that maps whether phrenic nerve capture occurred based on the acquired location information for the selected electrode configuration and the acquired location information for the selected other electrode configuration; and rendering the map and cardiac anatomical markers to a display to allow a user to observe a relationship between phrenic nerve stimulation and cardiac anatomy. Such a method may further include selecting an electrode configuration for chronic delivery of a cardiac pacing therapy based at least in part on the rendered map and cardiac anatomical markers. For example, consider rendering one or more contours to a display that indicate regions where phrenic nerve capture occurs or where phrenic nerve capture does not occur. Given such a map, a clinician may program an implantable device to avoid phrenic nerve capture or purposefully capture the phrenic nerve (e.g., programming an implantable cardiac pacing device with an electrode configuration suitable to deliver phrenic nerve stimulation responsive to sleep apnea).

An exemplary method can include executing a capture threshold assessment algorithm that automatically determines a phrenic nerve capture threshold value for a given electrode configuration. An exemplary method may include determining whether a patient experiences discomfort responsive to delivering cardiac pacing stimuli using one or more selected electrode configuration and generating a map that maps whether a patient experiences discomfort based on acquired location information for the one or more selected electrode configuration. Such a method may include determining whether a patient experience discomfort by receiving a signal from an actuator configured for actuation by a patient (e.g., a handheld actuator).

An exemplary system can include one or more processors; memory; and control logic configured to: select an electrode configuration for delivery of cardiac pacing stimuli where the electrode configuration includes at least one in vivo electrode; acquire location information for one or more of the at least one in vivo electrode of the selected electrode configuration; determine whether a phrenic nerve capture occurred responsive to delivering cardiac pacing stimuli using the selected electrode configuration; select another electrode configuration for delivery of cardiac pacing stimuli where the electrode configuration includes at least one in vivo electrode; acquire location information for one or more of the at least one in vivo electrode of the selected other electrode configuration; determine whether phrenic nerve capture occurred responsive to delivering cardiac pacing stimuli using the selected other electrode configuration; for the selected electrode configuration and the selected other electrode configuration, generate a map that maps whether phrenic nerve capture occurred based on the acquired location information for the selected electrode configuration and the acquired location information for the selected other electrode configuration; and render the map and cardiac anatomical markers to a display to allow a user to observe a relationship between phrenic nerve stimulation and cardiac anatomy. Such control logic may be stored as instructions on one or more computer-readable media (e.g., memory) and/or be implemented by one or more devices (e.g., an implanted device and an external device).

As mentioned, various techniques can map parameters germane to sensing. For example, FIG. 11 shows an exemplary method 1100 that can map sensing information associated with possible or potential configurations of an implantable device such as the device 100 of FIGS. 1 and 2.

In the method 1100, various blocks act to acquire sensed information or make determinations based on sensed information. Specifically, the method 1100 includes a R-wave acquisition block 1112, a far-field R-wave acquisition block 1122, a P-wave acquisition block 1132 and a P-wave to R-wave ratio determination block 1142. As described herein, the acquired information or determinations have associated location information as acquired by a localization system. The location information allows for mapping the acquired information or determinations with respect to cardiac anatomy.

In FIG. 11, each block includes some explanatory information such as a plot (e.g., IEGM). The block 1112 includes a plot of a R-wave, the block 1122 includes a plot of a far-field R-wave, the block 1132 includes a plot of a P-wave and the block 1142 includes a plot of a P-wave and an R-wave and a plot of a P-wave and a far-field R wave. While the blocks 1112, 1122, 1132 and 1142 refer to native or intrinsic events, a method may include one or more blocks for paced events or other aspects of a cardiac electrical signal morphology (e.g., T-wave, R-T interval, QRS width, evoked response morphology, etc.).

After acquisition of information, the method 1100 enters a mapping phase where individual maps may be generated. For example, as shown in the example of FIG. 11, a R-wave map block 1116 can generate a R-wave map (e.g., max/min amplitude, maximum derivative, R-wave width, signal-to-noise, etc.), a far-field R-wave map block 1126 can generate a far-field R-wave map (e.g., max/min amplitude, maximum derivative, R-wave width, signal-to-noise, etc.), a P-wave map block 1136 can generate a P-wave map (e.g., max/min amplitude, maximum derivative, P-wave width, signal-to-noise, etc.), and a ratio map block 1146 can generate a map of P-wave to R-wave amplitude ratio or other comparative characteristics. The map blocks 1116, 1126, 1136, 1146 may include instructions for rendering a map to a display device or to store sufficient data in memory for use by a rendering algorithm (e.g., to memory associated with a graphics processer unit (GPU)).

In the example of FIG. 11, as indicated in a composite map block 1150, which shows an example of a composite map, signal-to-noise ratio (S/N) is mapped for various regions of the heart 102. Specifically, five regions are shown with respect to S/N information. A left ventricular lateral wall region has contours for S/N associated with R-wave sensing greater than 4 and greater than 8. A posterior coronary sinus region has contours for S/N associated with left atrial P-wave sensing greater than 2 and greater than 4. Another posterior coronary sinus region has contours for S/N associated with R-wave sensing less than 1 (e.g., to be avoided for R-wave sensing). A right atrial region has a contour for S/N associated with far-field R-wave sensing greater than 2 and a contour for S/N associated with right atrial P-wave sensing greater than 6.

The method 1100 further includes a storage block 1170 that optionally stores one or more maps (e.g., one or more individual maps, a composite map, etc.). The storage block 1170 may store a map or maps (e.g., as localized data) to an implantable device, a PSA, a device programmer or a database. A stored map may be later used to assess patient condition, device condition, etc.

According to the method 1100, a clinician may view a composite S/N map on a display and appropriately select one or more configurations for chronic use by an implantable device that relies on sensing R-waves and/or P-waves.

The previously described exemplary system with selection mechanisms (e.g., touch screen, mouse, etc.) may be used to associate electrodes and sensed information to indicate whether an electrode can be used to adequate sense certain information. For example, in the composite map of FIG. 11, the clinician may disable R-wave sensing at all electrodes that do not lie within or lie adjacent a region with a S/N greater than 4. Such a process may involve setting a character in a field of a data table of an implantable device (e.g., field "R-sens": "0" disabled, "1" can be enabled). Once programmed in such a manner, during chronic operation, should a change in a sensing configuration be required, the implanted device may access the data table to determine whether sensing can be enabled for an alternative configuration. While the predictive value of the stored information may change over time, it may still be used to avert testing or otherwise ensure patient safety and optionally device longevity (e.g., by only selecting from electrode configurations that can sense certain desired information).

As described herein, an exemplary method includes: for each of a plurality of sensing configurations, acquiring a R-wave amplitude caused by delivery of a cardiac pacing stimulus; for each of the plurality of sensing configurations, acquiring a P-wave amplitude caused by delivery of a cardiac pacing stimulus; for each of the plurality of sensing configurations, acquiring location information sufficient to locate, in three-dimensions, at least one sensing electrode; generating a map that maps the acquired R-wave amplitudes and the acquired P-wave amplitudes based on the acquired location information; and rendering the map and cardiac anatomical markers to a display to allow a user to observe a relationship between R-wave sensing or P-wave sensing and cardiac anatomy. Such a method may include generating a map that maps ratios of P-wave amplitude to R-wave amplitude. Such a method may include mapping of far-field R-wave amplitudes, which may be intrinsic or due to paced activation (e.g., acquiring a far-field R-wave amplitude caused by delivery of a cardiac pacing stimulus).

An exemplary method can include, based on a rendered map and cardiac anatomical markers, deciding whether a sensing configuration allows for enabling an algorithm of an implantable cardiac pacing device. More generally, such a method may include selecting a sensing configuration, for sensing R-waves during chronic delivery of a cardiac pacing therapy, based at least in part on a rendered map and cardiac anatomical markers. Similarly, a method may include selecting a sensing configuration, for sensing P-waves during chronic delivery of a cardiac pacing therapy, based at least in part on a rendered map and cardiac anatomical markers or selecting a sensing configuration, for sensing R-waves and P-waves during chronic delivery of a cardiac pacing therapy, based at least in part on a rendered map and cardiac anatomical markers. Such methods may include rendering one or more contours to a display that include at least one qualification contour that indicates whether a qualification criterion or criteria for sensing an R-wave or a P-wave is met. Based on a map, a clinician may program an implantable cardiac therapy device to prohibit enabling an algorithm for one or more sensing configurations or to permit enabling an algorithm for one or more sensing configurations. Information may be communicated to an implantable device to automatically select or exclude a configuration or configurations.

An exemplary system can include one or more processors; memory; and control logic configured to: for each of a plurality of sensing configurations, acquire a R-wave amplitude caused by delivery of a cardiac pacing stimulus; for each of the plurality of sensing configurations, acquire a P-wave amplitude caused by delivery of a cardiac pacing stimulus; for each of the plurality of sensing configurations, acquire location information sufficient to locate, in three-dimensions, at least one sensing electrode; generate a map that maps the acquired R-wave amplitudes and the acquired P-wave amplitudes based on the acquired location information; and render the map and cardiac anatomical markers to a display to allow a user to observe a relationship between R-wave sensing or P-wave sensing and cardiac anatomy. Such control logic may be stored as instructions on one or more computer-readable media (e.g., memory) and/or be implemented by one or more devices (e.g., an implanted device and an external device).

As described herein, various maps can assist in decision making at the time of implant or after implant. Maps can include pacing parameter maps, sensing parameter maps or other parameter maps. As explained above, capture threshold is a pacing parameter that may be measured and mapped at various electrode locations. During an intraoperative procedure, a clinician may position and locate various electrodes (e.g., using a localization system) and execute an automatic capture algorithm to determine capture thresholds for the various electrodes. Such a procedure may be expedited by using starting values for the automatic capture algorithm based on one or more neighboring electrode sites (e.g., to reduce time required to find a capture threshold at each site). For example, consider the lead 106 of FIG. 1, the tip electrode 122 and the series of electrodes 123. An exemplary capture threshold assessment method may commence with the distal, tip electrode 122 and use a capture threshold value for the distal, tip electrode 122 as a starting value for a neighboring electrode (e.g., a distal electrode of the series of electrodes 123).

As mentioned, an exemplary method can include acquiring location information for electrodes, measuring pacing impedance for various electrode configurations that include at least some of the electrodes and mapping the pacing impedances on a map that includes anatomical markers of the heart. In this example, the pacing impedance may be determined at a constant voltage value for pacing output (or energy value) or it may be determined at a capture threshold value for pacing output.

Another pacing parameter is intrinsic or paced conduction delay, the latter of which may include pacing latency. For example, with respect to intrinsic conduction delay, an intrinsic event may be initially sensed at one location and latter sensed at one or more other locations. Where each of the locations corresponds to an electrode, a localization system may locate the electrodes to provide location information suitable for generating a map of the conduction delay or delays between the initial location and the one or more other locations.

In an example that includes pacing, pacing occurs using a selected electrode configuration and the emanating wavefront, corresponding evoked response or resulting evoked response is sensed using one or more different electrode configurations. Conduction delay values (e.g., in ms) may be determined as the time of delivery of a pacing stimulus to the time a waveform feature is detected at a location or locations associated with the one or more different electrode configurations as used for sensing. For example, a clinician may move an electrode-bearing lead or catheter to various locations within the coronary sinus of a patient; acquire location information for the locations using a localization system; delivery a pacing stimulus at each of the locations; and determine a conduction delay for each of the locations based on sensing a waveform for each of the locations where the waveform is associated with a respective pacing stimulus. In this example, sensing may occur via an electrode-bearing lead with a tip electrode fixed by a fixation mechanism (e.g., helix screw) in the apex of the right ventricle. Hence, given the time of delivery of the various pacing stimuli and detection times of a waveform feature of the sensed waveforms, an exemplary system may render a map on a display that shows the locations along with LV-RV conduction delays.

In another example, one or more pacing stimuli may be delivered using, at least in part, a remote, fixed electrode while sensing of associated waveform(s) occurs using a multi-electrode catheter or lead (e.g., positioned in the coronary sinus) where a localization system provides location information for the fixed electrode and the electrodes of the multi-electrode catheter or lead. In this example, or other examples, one or more sensed waveforms may be analyzed in real-time to detect an event or events or stored for later analysis by a routine of an exemplary mapping system that can determine a detection time or times for one or more events in each of the one or more sensed waveforms. Given location information, a delivery time or times and a detection time or times, a mapping application can generate a conduction time map suitable for rendering to a display.

In a particular example, the RV apex is paced repeatedly while moving an electrode-bearing lead to various locations within the coronary sinus of a patient where a localization system acquires location information sufficient to locate at least electrodes of the electrode-bearing lead. In turn, conduction times to each coronary sinus electrode location can be displayed on a map. While this example pertains to pacing, an exemplary method may rely on intrinsic rhythm and map, for example, sinus conduction delays to various electrode locations.

Another pacing parameter is phrenic nerve stimulation threshold, which, as explained, may be measured and mapped at various locations. For example, a clinician may move an electrode-bearing lead to various locations within the coronary sinus of a patient, acquire location information using a localization system, and deliver a high output pulse at each of the various locations. If none of the pulses capture the phrenic nerve, the output may be increased to determine a phrenic nerve capture threshold for each of the locations. In the instance that capture occurs, a mapping application may map the phrenic nerve capture threshold or thresholds for the various locations where phrenic nerve capture is possible (e.g., within an output pulse limit of an implantable pacing device). As mentioned, phrenic nerve capture can be determined via observation (e.g., by watching a patient's belly). An exemplary system may include an application that facilitates recording or otherwise noting that phrenic nerve capture occurred in response to a delivered stimulus or stimuli. Such an application may provide a user interface that include a control button on a display that can be actuated by touching (e.g., on a touch screen) or otherwise selecting the button (e.g., mouse, voice command, track ball, etc.).

In an alternative example, a phrenic stimulation threshold may be automatically determined at a point where a slew rate of a position signal, as measured by a localization system (e.g., ENSITE® NAVX® system), exceeds a predetermined threshold. In this example, upon phrenic nerve capture the patient's diaphragm will "jump" and one or more implanted electrodes will display similar jumps that can be detected by a localization system for locating electrodes. In yet another example, a patient may be fitted with an external or an implanted accelerometer positioned to detect movement related to respiration or a "hiccup" reflex caused by phrenic nerve actuation.

With respect to sensing parameter maps, as mentioned, sensing parameters such as R-wave amplitude may be measured and mapped at various electrode locations where a localization system provides location information for the electrode(s). An exemplary method can acquire one or more cardiac electrical signals and determine a single value of peak voltage for an R-wave, or alternatively determine an average or range of voltages over several cardiac cycles. As mentioned, P-wave amplitude may be measured and mapped at electrode locations where a localization system provides location information for the electrode(s). Similarly, far-field R-wave amplitude may be measured and mapped at electrode locations (e.g., for locations in or near the atria) where a localization system provides location information for the electrode(s).

As described herein, composite maps may be generated that rely on pacing, sensing or other parameters. Hence, a composite map may show only pacing parameters, only sensing parameters, only other parameters or a combination of any of pacing, sensing or other parameters. With respect to a composite map of sensing parameters, P-wave amplitude and far-field R-wave amplitude can be determined from localized P-wave data and localized far-field R-wave data to generate a composite map of, for example, ratios of P-wave amplitude to far-field R-wave amplitude. Such a composite map can advantageously show locations where device parameters relating to sensing, sensitivity, and discrimination may be optimally set. Such a composite map may also be used to elucidate locations in the coronary sinus proper (e.g., not necessarily within a tributary branch) that would be appropriate for left atrial sensing and pacing (e.g., for a single-pass, LV-LA lead).

As described herein, parameters other than pacing parameters and sensing parameters may be mapped. For example, an exemplary method can include maneuvering an electrode-bearing lead to various locations in the heart, delivering a high frequency current between electrodes on the lead and on another lead(s) (or between electrodes on the lead and a case of an implantable device). In turn, resulting cardiogenic or pulmonary impedance can be measured and displayed on a map at associated anatomic positions as determined by a localization system configured to locate implanted electrodes. In the foregoing example, such an impedance map can be used to place a lead in a position that provides acceptable impedance data, which may be used for chronic diagnostics or therapy optimization.

In another example, an exemplary method includes measuring impedance while pacing from an electrode-bearing lead and comparing the "paced" impedance with impedance measured during intrinsic rhythm. Given paced impedance and intrinsic impedance values, an impedance value ratio can be plotted on a map to determine, for example, a lead location that results in maximal sensitivity of cardiogenic or pulmonary impedance.

As described herein, other parameters suitable for mapping include potential measures (e.g., measured during intrinsic or pacing) that can be displayed on a map at associated anatomical positions. For example, the degree of fractionation of the electrogram, FFT of a single beat morphology, the regularity of the electrical activity, the stability of the electrical activity, changes in evoked response, etc., may be measured and mapped, individually or compositely.

Various exemplary composite maps are described herein. An algorithm for composite mapping can map at each location, two or more pacing, sensing, or other parameters. Such an algorithm may include a weighting function, for example, of the form $F=\Sigma a_i x_i^{n_i}$, that is computed for each location. In turn, a mapping application can include a selectable control (e.g., button, control box, etc.) to cause the value of the weighting function to be displayed on a map. In a particular example, coefficients of the foregoing weighting function can be designed to provide maximal pacemaker life, optimal arrhythmia discrimination, or other optimization goals. For example, a user can set a threshold for the composite value and any locations that are above the threshold value will be displayed in a manner that differentiates these locations from other locations (e.g., via color, flashing, etc.). An exemplary weighting function can combine values of two or more pacing, sensing or other parameters where a map can be generated to show the value of the weighting function with respect to anatomical locations.

Various exemplary techniques may be used to acquire location information or motion information (e.g., spatially for 1-D, 2-D or 3-D and, for motion, generally with respect to time). Electrodes may be positioned in the body and/or external to the body. Electrodes may be positioned within the pericardial space, as defined by the pericardium (e.g., in a vessel/chamber of the heart, etc.), and/or outside the pericardial space (e.g., consider the case electrode of the device 100 of FIGS. 1 and 2 or the surface patch electrodes of the system 500 of FIG. 5). Electrodes may be positioned at the pericardium, at the epicardial surface of the heart or between the pericardium and the epicardial surface of the heart. Electrodes may be implanted chronically or temporarily. Electrodes may optionally be suitable for stimulating the heart (e.g., pacing, shocking, etc.).

In an exemplary method to generate a map, a patient may have a basket catheter (e.g., a basket that at least partially surrounds the heart, an interchamber basket catheter such as the CONSTELLATION® catheter marketed by Boston Scientific, Natick, Mass. or other basket) that includes multiple splines. For a basket that partially surrounds the heart, such a basket can include splines spanning the circumference of the chamber. Such a basket may be placed in the intrapericardial space and include splines that are compliant and deform with the contraction and relaxation of the heart during a cardiac cycle to thereby capture motion of the myocardium. While two basket types of catheters have been mentioned, alternatively, a balloon catheter having multiple splines may be inserted into LV chamber via retrograde aortic access.

Exemplary External Programmer

Figure 12:
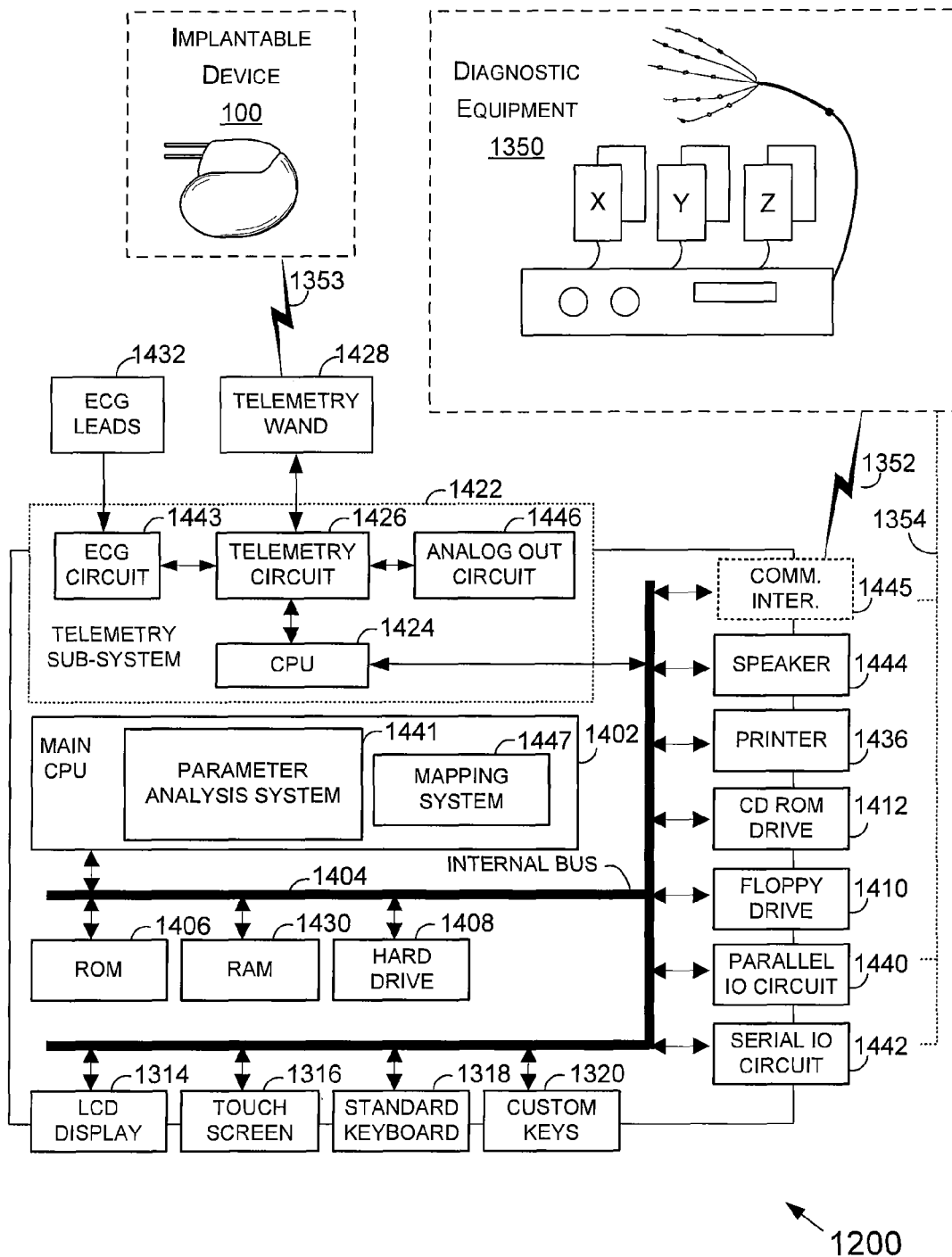
FIG. 12 is an exemplary system for acquiring information and analyzing such information.

FIG. 12 illustrates pertinent components of an external programmer 1200 for use in programming an implantable medical device 100 (see, e.g., FIGS. 1 and 2). The external programmer 1200 optionally receives information from other diagnostic equipment 1350, which may be a computing device capable of acquiring location information and other information. For example, the equipment 1350 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 1200 in distinguishing respiratory motion from cardiac.

Briefly, the programmer 1200 permits a clinician or other user to program the operation of the implanted device 100 and to retrieve and display information received from the implanted device 100 such as IEGM data and device diagnostic data. Where the device 100 includes a module such as the position detection module 239, then the programmer 1200 may instruct the device 100 to measure potentials and to communicate measured potentials to the programmer via a communication link 1353. The programmer 1200 may also instruct a device or diagnostic equipment to deliver current to generate one or more potential fields within a patient's body where the implantable device 100 may be capable of measuring potentials associated with the field(s).

The external programmer 1200 may be configured to receive and display ECG data from separate external ECG leads 1432 that may be attached to the patient. The programmer 1200 optionally receives ECG information from an ECG unit external to the programmer 1200. As already mentioned, the programmer 1200 may use techniques to account for respiration.

Depending upon the specific programming, the external programmer 1200 may also be capable of processing and analyzing data received from the implanted device 100 and from ECG leads 1432 to, for example, render diagnosis as to medical conditions of the patient or to the operations of the implanted device 100. As noted, the programmer 1200 is also configured to receive data representative of conduction time delays from the atria to the ventricles and to determine, there-from, an optimal or preferred location for pacing. Further, the programmer 1200 may receive information such as ECG information, IEGM information, information from diagnostic equipment, etc., and determine one or more parameter (e.g., consider the method 300).

Now, considering the components of programmer 1200, operations of the programmer are controlled by a CPU 1402, which may be a generally programmable microprocessor or microcontroller or may be a dedicated processing device such as an application specific integrated circuit (ASIC) or the like. Software instructions to be performed by the CPU are accessed via an internal bus 1404 from a read only memory (ROM) 1406 and random access memory 1430. Additional software may be accessed from a hard drive 1408, floppy drive 1410, and CD ROM drive 1412, or other suitable permanent or removable mass storage device. Depending upon the specific implementation, a basic input output system (BIOS) is retrieved from the ROM 1406 by CPU 1402 at power up. Based upon instructions provided in the BIOS, the CPU 1402 "boots up" the overall system in accordance with well-established computer processing techniques.

Once operating, the CPU 1402 displays a menu of programming options to the user via an LCD display 1314 or other suitable computer display device. To this end, the CPU 1402 may, for example, display a menu of specific programming parameters of the implanted device 100 to be programmed or may display a menu of types of diagnostic data to be retrieved and displayed. In response thereto, the clinician enters various commands via either a touch screen 1316 overlaid on the LCD display or through a standard keyboard 1318 supplemented by additional custom keys 1320, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to the determination of an optimal location for pacing, sensing, etc., CPU 1402 includes a parameter analysis system 1441 and a 3-D mapping system 1447. The systems 1441 and 1447 may receive information from the implantable device 100 and/or diagnostic equipment 1350. The parameter analysis system 1441 optionally includes control logic to associate information and to make one or more conclusions based on a map of a parameter or parameters (e.g., consider the block 330 of FIG. 3).

Where information is received from the implanted device 100, a telemetry wand 1428 may be used. Other forms of wireless communication exist as well as forms of communication where the body is used as a "wire" to communicate information from the implantable device 100 to the programmer 1200.

If information is received directly from diagnostic equipment 1350, any appropriate input may be used, such as parallel IO circuit 1440 or serial IO circuit 1442. Motion information received via the device 100 or via other diagnostic equipment 1350 may be analyzed using the mapping system 1447. In particular, the mapping system 1447 (e.g., control logic) may identify positions within the body of a patient and associate such positions with one or more electrodes where such electrodes may be capable of delivering stimulation energy to the heart.

A communication interface 1445 optionally allows for wired or wireless communication with diagnostic equipment 1350 or other equipment. The communication interface 1445 may be a network interface connected to a network (e.g., intranet, Internet, etc.).

A map or model of cardiac motion may be displayed using display 1314 based, in part, on 3-D heart information and optionally 3-D torso information that facilitates interpretation of motion information. Such 3-D information may be input via ports 1440, 1442, 1445 from, for example, a database, a 3-D imaging system, a 3-D location digitizing apparatus (e.g., stereotactic localization system with sensors and/or probes) capable of digitizing the 3-D location. According to such an example, a clinician can thereby view the optimal location for delivery of stimulation energy on a map of the heart to ensure that the location is acceptable before an electrode or electrodes are positioned and optionally fixed at that location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 1200 optionally records procedures and allows for playback (e.g., for subsequent review). For example, a heart map and all of the electrical activation data, mechanical activation data, parameter data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 1422 may include its own separate CPU 1424 for coordinating the operations of the telemetry subsystem. In a dual CPU system, the main CPU 1402 of programmer communicates with telemetry subsystem CPU 1424 via internal bus 1404. Telemetry subsystem additionally includes a telemetry circuit 1426 connected to telemetry wand 1428, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 1200 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 1200 (e.g., within a random access memory (RAM) 1430, hard drive 1408, within a floppy diskette placed within floppy drive 1410). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 1200 has a communication link to an external storage device or network storage device, then information may be stored in such a manner (e.g., on-site database, off-site database, etc.). The programmer 1200 optionally receives data from such storage devices.

A typical procedure may include transferring all patient and device diagnostic data stored in an implanted device 100 to the programmer 1200. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 1422 receives ECG signals from ECG leads 1432 via an ECG processing circuit 1434. As with data retrieved from the implanted device 100, signals received from the ECG leads are stored within one or more of the storage devices of the programmer 1200. Typically, ECG leads output analog electrical signals representative of the ECG. Accordingly, ECG circuit 1434 includes analog to digital conversion circuitry for converting the signals to digital data appropriate for further processing within programmer 1200. Depending upon the implementation, the ECG circuit 1443 may be configured to convert the analog signals into event record data for ease of processing along with the event record data retrieved from the implanted device. Typically, signals received from the ECG leads 1432 are received and processed in real time.

Thus, the programmer 1200 is configured to receive data from a variety of sources such as, but not limited to, the implanted device 100, the diagnostic equipment 1350 and directly or indirectly via external ECG leads (e.g., subsystem 1422 or external ECG system). The diagnostic equipment 1350 includes wired 1354 and/or wireless capabilities 1352 which optionally operate via a network that includes the programmer 1200 and the diagnostic equipment 1350 or data storage associated with the diagnostic equipment 1350.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 1402, the programming commands are converted to specific programming parameters for transmission to the implanted device 100 via telemetry wand 1428 to thereby reprogram the implanted device 100 or other devices, as appropriate.

Prior to reprogramming specific parameters, the clinician may control the external programmer 1200 to display any or all of the data retrieved from the implanted device 100, from the ECG leads 1432, including displays of ECGs, IEGMs, statistical patient information (e.g., via a database or other source), diagnostic equipment 1350, etc. Any or all of the information displayed by programmer may also be printed using a printer 1436.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 1200 optionally includes a modem to permit direct transmission of data to other programmers via the public switched telephone network (PSTN) or other interconnection line, such as a T1 line or fiber optic cable. Depending upon the implementation, the modem may be connected directly to internal bus 1404 may be connected to the internal bus via either a parallel port 1440 or a serial port 1442.

Other peripheral devices may be connected to the external programmer via the parallel port 1440, the serial port 1442, the communication interface 1445, etc. Although one of each is shown, a plurality of input output (IO) ports might be provided. A speaker 1444 is included for providing audible tones to the user, such as a warning beep in the event improper input is provided by the clinician. Telemetry subsystem 1422 additionally includes an analog output circuit 1446 for controlling the transmission of analog output signals, such as IEGM signals output to an ECG machine or chart recorder.

With the programmer 1200 configured as shown, a clinician or other user operating the external programmer is capable of retrieving, processing and displaying a wide range of information received from the ECG leads 1432, from the implanted device 100, the diagnostic equipment 1350, etc., and to reprogram the implanted device 100 or other implanted devices if needed. The descriptions provided herein with respect to FIG. 12 are intended merely to provide an overview of the operation of programmer and are not intended to describe in detail every feature of the hardware and software of the device and is not intended to provide an exhaustive list of the functions performed by the device.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A system comprising:
   one or more processors;
   memory; and
   control logic configured to:
      select an electrode configuration for delivery of cardiac pacing stimuli wherein the electrode configuration comprises at least one in vivo electrode;
      acquire location information for one or more of the at least one in vivo electrode of the selected electrode configuration;
      determine a capture threshold value responsive to delivering cardiac pacing stimuli using the selected electrode configuration;
      select another electrode configuration for delivery of cardiac pacing stimuli wherein the electrode configuration comprises at least one in vivo electrode;
      acquire location information for one or more of the at least one in vivo electrode of the selected other electrode configuration;
      determine a capture threshold value responsive to delivering cardiac pacing stimuli using the selected other electrode configuration;
      for the selected electrode configuration and the selected other electrode configuration, generate a map that maps the corresponding capture threshold values onto a diagram of cardiac anatomy based on the acquired location information for the selected electrode configuration and the acquired location information for the selected other electrode configuration; and render the map and cardiac anatomical markers to a display to present, on the diagram, a relationship between the capture threshold values and the cardiac anatomy.

2. The system of claim 1 wherein the control logic is further configured to select an electrode configuration for chronic delivery of a cardiac pacing therapy based at least in part on the rendered map and cardiac anatomical markers.

3. The system of claim 1 wherein, to determine a capture threshold, the control logic is configured to execute a capture threshold assessment algorithm that automatically determines a capture threshold value for a given electrode configuration.

4. The system of claim 1 wherein, to render the map, the control logic is configured to render one or more capture threshold contours onto the cardiac anatomy to the display.

5. The system of claim 1 wherein the control logic is configured to, for the selected electrode configuration and the selected other electrode configuration, determine maturation compensated capture threshold values.

6. The system of claim 1 further comprising a storage for storing the map, wherein the storage is accessible by an implantable device programmer.

7. The system of claim 1 wherein the cardiac anatomical markers comprise ventricular markers, atrial markers or ventricular markers and atrial markers.

8. The system of claim 1, wherein the control logic is configured to present the map of the capture threshold values with respect to the diagram of the cardiac anatomy and with respect to a position of at least one electrode on at least one lead.

9. A system comprising:
one or more processors;
memory; and
control logic configured to:
 select an electrode configuration for delivery of cardiac pacing stimuli wherein the electrode configuration comprises at least one in vivo electrode;
 acquire location information for one or more of the at least one in vivo electrode of the selected electrode configuration;
 determine a capture threshold value responsive to delivering cardiac pacing stimuli using the selected electrode configuration;
 select another electrode configuration for delivery of cardiac pacing stimuli wherein the electrode configuration comprises at least one in vivo electrode;
 acquire location information for one or more of the at least one in vivo electrode of the selected other electrode configuration;
 determine a capture threshold value responsive to delivering cardiac pacing stimuli using the selected other electrode configuration;
 for the selected electrode configuration and the selected other electrode configuration, qenerate a map that maps the corresponding capture threshold values based on the acquired location information for the selected electrode configuration and the acquired location information for the selected other electrode configuration; and
 render the map and cardiac anatomical markers to a display to allow a user to observe a relationship between capture threshold and cardiac anatomy;
wherein the control logic is further configured to determine current drain values based on the capture threshold values and generate a map that maps the current drain values based on the acquired location information for the selected electrode configuration and the acquired location information for the selected other electrode configuration.

10. The method of claim 9 wherein, to determine current drain values, the control logic is further configured to determine each current drain value based at least in part on an electrode impedance value for a given electrode configuration.

\* \* \* \* \*